(12) United States Patent
Parthasarathy et al.

(10) Patent No.: US 7,981,600 B2
(45) Date of Patent: Jul. 19, 2011

(54) METHODS AND DEVICES FOR REMOVAL OF ORGANIC MOLECULES FROM BIOLOGICAL MIXTURES USING AN ANION EXCHANGE MATERIAL THAT INCLUDES A POLYOXYALKYLENE

(75) Inventors: Ranjani V Parthasarathy, Woodbury, MN (US); Rusty A. Rasmussen, Hudson, WI (US)

(73) Assignee: 3M Innovative Properties Company, St. Paul, MN (US)

( * ) Notice: Subject to any disclaimer, the term of this patent is extended or adjusted under 35 U.S.C. 154(b) by 1357 days.

(21) Appl. No.: 10/417,609

(22) Filed: Apr. 17, 2003

(65) Prior Publication Data
US 2004/0209258 A1   Oct. 21, 2004

(51) Int. Cl.
*C12Q 1/68* (2006.01)
(52) U.S. Cl. .......................................................... 435/6
(58) Field of Classification Search .................. None
See application file for complete search history.

(56) References Cited

U.S. PATENT DOCUMENTS

| | | | |
|---|---|---|---|
| 3,157,635 A | 11/1964 | Tanaka et al. .............. 260/211.5 |
| 4,399,009 A | 8/1983 | Chisholm |
| 4,399,235 A | 8/1983 | Raley, Jr. et al. |
| 4,780,367 A | 10/1988 | Lau et al. |
| 4,923,978 A | 5/1990 | McCormick |
| 5,183,705 A | 2/1993 | Birkholz et al. |
| 5,187,066 A | 2/1993 | Becker et al. |
| 5,294,668 A | 3/1994 | Babu |
| 5,334,316 A | 8/1994 | Bruening et al. |
| 5,380,901 A | 1/1995 | Antonucci et al. |
| 5,620,663 A | 4/1997 | Aysta et al. |
| 5,633,290 A | 5/1997 | Frechet et al. |
| 5,741,828 A | 4/1998 | Stoy et al. |
| 5,801,237 A | 9/1998 | Johansson |
| 5,834,583 A | 11/1998 | Hancock et al. |
| 5,856,379 A * | 1/1999 | Shiratsuchi et al. .......... 523/209 |
| 5,869,002 A | 2/1999 | Limon et al. |
| 5,997,818 A | 12/1999 | Hacker et al. |
| 6,007,690 A | 12/1999 | Nelson et al. |
| 6,048,550 A | 4/2000 | Chan et al. |
| 6,063,838 A | 5/2000 | Patnode et al. |
| 6,071,406 A | 6/2000 | Tsou |
| 6,074,827 A | 6/2000 | Nelson et al. |
| 6,093,558 A | 7/2000 | Seed et al. |
| 6,103,199 A | 8/2000 | Bjornson et al. |
| 6,143,247 A | 11/2000 | Sheppard, Jr. et al. |
| 6,168,948 B1 * | 1/2001 | Anderson et al. .......... 435/287.2 |
| 6,197,595 B1 | 3/2001 | Anderson et al. |
| 6,265,168 B1 * | 7/2001 | Gjerde et al. .................. 435/6 |
| 6,277,488 B1 | 8/2001 | Kobe et al. |
| 6,284,113 B1 | 9/2001 | Bjornson et al. |
| 6,306,273 B1 | 10/2001 | Wainright et al. |
| 6,319,469 B1 | 11/2001 | Mian et al. |
| 6,344,326 B1 * | 2/2002 | Nelson et al. .................. 435/6 |
| 6,383,783 B1 | 5/2002 | Bruni et al. |
| 6,450,047 B2 | 9/2002 | Swedberg et al. |
| 6,451,260 B1 | 9/2002 | Düsterhöft et al. |
| 6,504,021 B2 * | 1/2003 | Kristyanne et al. .......... 536/23.1 |
| 6,617,136 B2 | 9/2003 | Parthasarathy et al. |
| 6,627,159 B1 | 9/2003 | Bedingham et al. |
| 6,632,399 B1 | 10/2003 | Kellogg et al. |
| 6,734,401 B2 | 5/2004 | Bedingham et al. |
| 6,814,935 B2 | 11/2004 | Harms et al. |
| 7,026,168 B2 | 4/2006 | Bedingham et al. |
| 7,192,560 B2 | 3/2007 | Parthasarathy et al. |
| 2001/0045000 A1 | 11/2001 | Gundel et al. |
| 2002/0001848 A1 | 1/2002 | Bedingham et al. |
| 2002/0046966 A1 | 4/2002 | Muscate-Magnussen |
| 2002/0047003 A1 | 4/2002 | Bedingham et al. |
| 2002/0048533 A1 | 4/2002 | Harms et al. |
| 2002/0064885 A1 | 5/2002 | Bedingham et al. |
| 2002/0182114 A1 | 12/2002 | Ingenhoven et al. |
| 2003/0013203 A1 | 1/2003 | Jedrzejewski et al. |
| 2003/0017551 A1 | 1/2003 | Parthasarathy et al. |
| 2003/0017567 A1 | 1/2003 | Parthasarathy et al. |
| 2003/0053934 A1 | 3/2003 | Andersson et al. |
| 2003/0062310 A1 | 4/2003 | Zare et al. |
| 2003/0120062 A1 | 6/2003 | Parthasarathy et al. |
| 2003/0138779 A1 | 7/2003 | Parthasarathy et al. |
| 2003/0228706 A1 | 12/2003 | Ramstad et al. |
| 2004/0016702 A1 | 1/2004 | Hennessy et al. |
| 2004/0018116 A1 | 1/2004 | Desmond et al. |
| 2004/0018559 A1 | 1/2004 | Lau et al. |
| 2004/0209258 A1 | 10/2004 | Parthasarathy et al. |
| 2006/0013732 A1 | 1/2006 | Parthasarathy et al. |
| 2008/0103297 A1 | 5/2008 | Parthasarathy et al. |

FOREIGN PATENT DOCUMENTS

DE          197 31 670 A1      1/1999

(Continued)

OTHER PUBLICATIONS

"ABI Prism® BigDye™ Terminators v3.0 Cycle Sequencing Kit," product information [online]. Applied Biosystems, 2000, 2001 [retrieved Dec. 3, 2001]. Retrieved from the Internet: <URL:http://www.appliedbiosystems.com/products/productdetail.cfm?id=81>, p. 1.

(Continued)

*Primary Examiner* — Heather Calamita
(74) *Attorney, Agent, or Firm* — Nicole J. Einerson

(57) ABSTRACT

Methods and devices for removing small negatively charged molecules from a biological sample mixture that uses an anion exchange material that has associated therewith a polyoxyalkylene.

51 Claims, 4 Drawing Sheets

FOREIGN PATENT DOCUMENTS

| | | |
|---|---|---|
| DE | 197 31 670 C2 | 6/2000 |
| EP | 0 309 259 A2 | 3/1989 |
| EP | 0 309 259 A3 | 3/1989 |
| EP | 0 409 432 A2 | 1/1991 |
| EP | 0 409 432 A3 | 1/1991 |
| EP | 0 426 488 A1 | 5/1991 |
| EP | 0 447 362 A1 | 9/1991 |
| EP | 0 309 259 B1 | 6/1994 |
| EP | 0 426 488 B1 | 4/1997 |
| JP | 7-265718 | 10/1995 |
| WO | WO 92/16659 | 10/1992 |
| WO | WO 95/24505 A1 | 9/1995 |
| WO | WO 97/27325 A1 | 7/1997 |
| WO | WO 97/27325 A3 | 7/1997 |
| WO | WO 98/04909 A1 | 2/1998 |
| WO | WO 98/12351 A1 | 3/1998 |
| WO | WO 98/39094 * | 11/1998 |
| WO | WO 99/15876 A1 | 4/1999 |
| WO | WO 99/15888 A1 | 4/1999 |
| WO | WO 99/39120 A1 | 8/1999 |
| WO | WO 99/40174 A1 | 8/1999 |
| WO | WO 99/46591 A2 | 9/1999 |
| WO | WO 99/46591 A3 | 9/1999 |
| WO | WO 99/58664 A1 | 11/1999 |
| WO | WO 00/45180 A1 | 8/2000 |
| WO | WO 00/62051 A2 | 10/2000 |
| WO | WO 00/62051 A3 | 10/2000 |
| WO | WO 00/68336 A1 | 11/2000 |
| WO | WO 01/03149 A1 | 1/2001 |
| WO | WO 01/12327 A1 | 2/2001 |
| WO | WO 01/21632 A1 | 3/2001 |
| WO | WO 01/25490 A1 | 4/2001 |
| WO | WO 01/25491 A1 | 4/2001 |
| WO | WO 01/38516 | 5/2001 |
| WO | WO 01/38865 | 5/2001 |
| WO | WO 01/62976 | 8/2001 |
| WO | WO 01/68240 A2 | 9/2001 |
| WO | WO 01/68240 A3 | 9/2001 |
| WO | WO 01/68913 | 9/2001 |
| WO | WO 01/71732 A2 | 9/2001 |
| WO | WO 01/71732 A3 | 9/2001 |
| WO | WO 03/054509 A2 | 7/2003 |
| WO | WO 03/054509 A3 | 7/2003 |
| WO | WO 2004/009851 A2 | 1/2004 |
| WO | WO 2004/010760 A2 | 2/2004 |
| WO | WO 2004/011141 A1 | 2/2004 |
| WO | WO 2004/011142 A1 | 2/2004 |
| WO | WO 2004/011592 A2 | 2/2004 |
| WO | WO 2004/011681 A1 | 2/2004 |

OTHER PUBLICATIONS

American Society of Testing Materials, "ASTM D 570-98, Standard Test Method for Water Absorption of Plastics," *Annual Book of ASTM Standards*, pp. 32-35, Publication page, and Title page (2003).

"AutoSeq96 Dye Terminator Clean-up Kit / Adapter Plate for AutoSeq96," product catalogue [online]. Amersham Biosciences, 2001 [retrieved Dec. 3, 2003]. Retrieved from the Internet: <URL:http://www.apbiotech.com/stiboasp/showmodule.asp?nModuleid=164360 >, pp. 1-2.

"BLAST," National Institutes of Health [online] United States, [retrieved Oct. 23, 2000]. Retrieved from the Internet:<URL:http://www.ncbi.nlm.nih.gov/BLAST>, 2 pgs.

Boom et al., "Rapid and Simple Method for Purification of Nucleic Acids," *Journal of Clinical Microbiology*, Mar. 1990; vol. 28, No. 3; pp. 495-503, Publication page, and Title page.

"Porex Corporate Profile," [online]. Porex Corporation, 2001 [retrieved Dec. 5, 2001]. Retrieved from the Internet: <URL:http://www.porex.com/english/corporate/index.asp>, pp. 1-3.

"Porex Products Group," product profile [online]. Porex Corporation, 2001 [retrieved Dec. 5, 2001]. Retrieved from the Internet: <URL:http://www.porex.com/english/porous/index.asp>, pp. 1-2.

"Purification so fast it'll make your head spin: RapTract Dye Terminator Removal Kit," Prolinx Product Information, Bothell, WA, 2000. pp. 1-6.

"3M Empore Products 96-Well Plates," product listing [online]. 3M Corporation, 1999 [retrieved Dec. 5, 2001]. Retrieved from the Internet: <URL:http//www.mmm.com/empore/formats/Plates/sorbavlb/index/htm>, pp. 1-2.

"3M Empore Products Empore 96-Well Plates" SPE Extraction Disk Plates & Filter Plates, 3M Extraction Disk Plates for SPE, product listing [online]. 3M Corporation, 1999 [retrieved Dec. 5, 2001]. Retrieved from the Internet: <URL:http://www.mmm.com/empore/formats/Plates/index.htm>, pp. 1-2.

Takeuchi et al., "Ion Chromatography Using Anion Exchangers Modified with Anionic Polysaccharides," LCGC Magazine [online]. LCGC North America, 2001 [retrieved Oct. 2, 2001]. Retrieved from the Internet: <URL:http://www.lcgcmag.com/articles/0004_articles/0004_Takeuchi/0004_Takeuchi.asp>, pp. 1-12.

Tong, et al., "Solid-Phase Method for the Purification of DNA Sequencing Reactions," *Anal Chem*, 1992; vol. 64, No. 22; pp. 2672-2677, Publication page, and Title page.

Whelan, Tony, Msc, Consultant, *Polymer Technology Dictionary*, Chapman and Hall, London, UK, 1994; Title page, Publication page, Table of Contents, and pp. 322, 326, and 335 (6 pgs. total). (Exhibit A).

U.S. Appl. No. 09/841,264, filed Apr. 24, 2001, Parthasarathy et al.
U.S. Appl. No. 09/841,272, filed Apr. 24, 2001, Parthasarathy et al.
U.S. Appl. No. 09/894,810, filed Jun. 28, 2001, Bedingham et al.
U.S. Appl. No. 09/895,001, filed Jun. 28, 2001, Harms et al.
U.S. Appl. No. 09/895,010, filed Jun. 28, 2001, Bedingham et al.
U.S. Appl. No. 10/027,226, filed Dec. 20, 2001, Parthasarathy et al.
U.S. Appl. No. 11/226,161, filed Sep. 14, 2005, Parthasarathy et al.

Daughton, "Quantitation of Acrylamide (and Polyacrylamide): Critical review of methods for trace determination/formulation analysis & Future-research recommendations," Final Report No. CGD-02/88, prepared for The California Public Health Foundation, Berkeley, CA, Jun. 23, 1988; Title page, Table of Contents (4 pgs), and 58 pgs (63 pgs total).

"Using Ion Exchange Chromatography to Separate Proteins" datasheet [online]. Access Excellence Activities Exchange @ the National Health Museum, Washington, D.C., 2007 [retrieved on Feb. 28, 2007]. Retrieved from the Internet:<URL:http://cf.acessexcellence.org/AE/AEC/AEF/1994/daugherty_ion.html>; 4pgs.

Villee, "Biology," Seventh Edition, W. B. Saunders Company, Philadelphia, PA, 1977; Title page, Publication page, and p. 877 (3 pgs).

* cited by examiner

US 7,981,600 B2

METHODS AND DEVICES FOR REMOVAL OF ORGANIC MOLECULES FROM BIOLOGICAL MIXTURES USING AN ANION EXCHANGE MATERIAL THAT INCLUDES A POLYOXYALKYLENE

BACKGROUND

Water-soluble dyes (e.g., fluorescent, chemiluminescent, visible, and near-IR) are used routinely in molecular biology to label and monitor components of biological reactions. Frequently, residual dyes as well as other organic molecules should be removed before proceeding with many downstream applications. Thus, the present invention is directed to removing dyes and other organic molecules from biological mixtures, particularly in low volume, microfluidic devices.

There is a significant need for high throughput, low volume, integrated microfluidic devices in order to increase sample throughput and reduce the amount of reagents used per sample (thereby reducing cost per sample) in biological reactions. Small volume Polymerase Chain Reaction (PCR) and nucleic acid cycle sequencing reactions are examples of standard molecular biology techniques that are suitable for incorporation into miniaturized formats. In both applications, removal of residual primers, nucleic acid templates, dyes, and other organic molecules are generally necessary prior to any further downstream applications.

One example where such removal methods are used is in the preparation of a finished sample (e.g., purified nucleic acid materials) from a starting sample (e.g., a raw sample such as blood, bacterial lysate, etc.). For example, to obtain a purified sample of the desired materials in high concentrations, the starting sample is typically prepared for PCR after which the PCR process is performed to obtain a desired common PCR reaction product. The common PCR reaction product can then be used in a variety of molecular biological applications, including, for example, sequencing, cloning, genotyping, and forensic applications.

In fluorescence-based DNA sequencing applications, unincorporated dye terminators (i.e., dye-labeled dideoxy terminators such as dideoxynucleotide triphosphates (ddNTPs)) should preferably be removed from the reaction mixture prior to analysis of the DNA sequence fragments. Failure to sufficiently reduce the concentration of dye terminator molecules leads to dye artifacts (i.e., other dye-containing molecules such as dye-labeled dideoxy terminators such as dideoxynucleotide diphosphates (ddNDPs), dideoxynucleotide monophosphates (ddNMPs), and dideoxynucleosides) that can significantly obscure DNA sequence information. Sequencing reaction purification is a desired step in the preparation of samples prior to sequence analysis, particularly when using a capillary electrophoresis (CE) sequencer.

Conventionally, after completion of the PCR or cycle sequencing reaction, the product is generally purified by either alcohol (ethanol or isopropanol) precipitation or gel filtration chromatography. Other protocols using polyalkylene glycol and biotin-streptavidin interactions have also been utilized for sequencing reaction clean-up. Ultrafiltration membranes, phenol/chloroform extraction, and enzymatic treatments are other methods that are commonly used for purification of PCR and sequencing reaction mixtures.

Such conventional technologies for the purification of PCR and nucleic acid sequencing reactions have not proven to be suitable for incorporation into a microfluidic device. Alcohol precipitation utilizes volatile and flammable reagents. Hydrogels (e.g., crosslinked dextrans), commonly used in size exclusion chromatography, require large bed volumes (10× relative the volume of sample) for efficient separation of impurities from product. Gels are first swollen with a relatively large volume of water, centrifuged, and loaded substantially immediately, because, upon dehydration, these materials are prone to cracking. Biotin-streptavidin mediated purifications require the use of custom biotinylated primers for the efficient capture of product. Biotinylated products are generally captured onto streptavidin-treated paramagnetic particles and physically separated from impurities with the use of a magnet. Alternatively, hybridization based purification (HBP) of the PCR or nucleic acid sequencing product can be accomplished by utilizing primers containing specially designed capture tags. Separation of the nucleic acid fragment from the biological matrix can be achieved by hybridization of the capture tag to a complementary strand bound to a solid support. Both the biotin and HBP strategies would require a rinsing step followed by elution of the sequencing or PCR product from the substrate. Although biotin-streptavidin and HBP purification methods yield clean PCR and sequencing fragments, both approaches require customized primers, which can be cumbersome and expensive.

An alternative approach for the removal of residual dye terminators from DNA sequencing reactions involves treating the reaction mixture with an enzyme (e.g., shrimp alkaline phosphatase) to dephosphorylate residual nucleotide triphosphates. Although cleavage of the phosphate groups(s) from the dye-labeled dideoxynucleotide triphosphates alters the mobility of the dye-labeled nucleotides in the sequencing gel, residual dye moieties are not removed from the reaction mixture by this procedure and must still be eliminated prior to injection of the sample into the sequencer. This is generally accomplished by subsequent alcohol precipitation of the digested product.

PCR and sequencing products can also be effectively purified by adsorption of nucleic acid fragments onto beads and silica gel membranes using chaotropic agents. Impurities (e.g., residual primers, dyes, and salts) can be rinsed from the substrate and the purified product eluted. This multi-step bind/rinse/elute purification scheme may also prove to be cumbersome within the context of a microfluidic device.

Yet another method of removing unwanted materials (e.g., dyes) from cycle sequencing (e.g., Sanger cycling) reaction mixtures involves the use of paramagnetic particles. One example of suitable paramagnetic particles incorporating dye terminator removal materials is available under the trade designation RAPXTRACT from Prolinx Inc., Bothell, Wash. Further examples of these materials (and their methods of use) may be found in U.S. patent application Publication No. US 2002/0047003 A1 published on Apr. 25, 2002 and entitled ENHANCED SAMPLE PROCESSING DEVICES SYSTEMS AND METHODS. Unfortunately, however, with such particles, the particles must remain in a hydrated state, which limits the ability to prefabricate particle-loaded devices.

Thus, methods are needed for the removal of dyes and other organic molecules from biological mixtures, such as nucleic acid amplification reaction mixtures (e.g., PCR or cycle sequencing reaction mixtures).

SUMMARY OF THE INVENTION

The present invention provides methods for processing biological mixtures, i.e., samples containing a biological material such as peptide- and/or nucleotide-containing material. Specifically, the present invention provides methods for the removal of negatively charged organic molecules (e.g., dyes, primers, probes, dNTPs, dye terminators such as ddNTPs, ddNDPs, ddNMPs and nucleosides) from biological sample mixtures using anion exchange materials having associated therewith a polyoxyalkylene. These methods are based on solid-phase extraction techniques. They are advantageous because they can be incorporated into high throughput, low volume, integrated microfluidic devices, if desired, particularly those being developed for PCR and DNA sequencing.

The present invention provides methods of removing small negatively charged organic molecules from a biological sample mixture. Preferably, the biological sample mixture is a biological sample mixture such as a nucleic acid amplification reaction mixture (e.g., a PCR reaction mixture or a nucleic acid sequencing reaction mixture).

Herein, "removal" of unwanted molecules involves adhering such molecules to the solid-phase material and allowing desirable products to remain in solution. This is in contrast to conventional elution methods that involve adhering the desirable products to the solid-phase material, washing away the unwanted molecules, and eluting the desirable products to remove them from the solid-phase material.

For each of the embodiments described herein, the anion exchange material includes (i.e., has associated therewith) a polyoxyalkylene.

In one embodiment, a method includes: providing a surface that includes an anion exchange material; providing a biological sample mixture comprising small negatively charged organic molecules having a molecular weight of less than about 6,000; wherein the biological sample mixture is selected from the group consisting of a nucleic acid amplification reaction mixture (e.g., a PCR reaction mixture or a sequencing reaction mixture) and a nucleic acid labeling reaction mixture; and contacting the biological sample mixture with the surface that includes the anion exchange material to remove at least a portion of the small negatively charged organic molecules from the biological sample mixture.

In another embodiment, a method includes: providing a surface that includes an anion exchange material (preferably, including quaternized nitrogen-containing groups such as quaternary ammonium ions) partially coated with a negatively charged polymer (preferably, a polyelectrolyte); providing a biological sample mixture (e.g., a nucleic acid amplification reaction mixture); and contacting the biological sample mixture with the surface that includes an anion exchange material partially coated with a negatively charged polymer to remove at least a portion of the small negatively charged organic molecules from the biological sample mixture.

In another embodiment, a method includes: providing a device (e.g., a microfluidic device) that includes at least one process array that has a surface that includes an anion exchange material; providing a biological sample mixture in the at least one process array, wherein the biological sample mixture includes small negatively charged organic molecules having a molecular weight of less than about 6,000; and transferring the biological sample mixture within the at least one process array, wherein the biological sample mixture and the surface having an anion exchange material remain in contact for a sufficient time to remove at least a portion of the small negatively charged organic molecules from the biological sample mixture.

In yet another embodiment, a method includes: providing a device that includes at least one process array that has a surface including an anion exchange material (preferably, quaternary ammonium ions) partially coated with a negatively charged polymer (preferably, a polyelectrolyte); providing a biological sample mixture in the at least one process array; and transferring the biological sample mixture within the at least one process array, wherein the biological sample mixture and the surface including an anion exchange material partially coated with a negatively charged polymer remain in contact for a sufficient time to remove at least a portion of the small negatively charged molecules from the biological sample mixture.

When the biological sample mixture is a sequencing reaction mixture, the small negatively charged molecules are typically selected from the group consisting of dye-labeled terminators, primers, degraded dye molecules, deoxynucleotide triphosphates, and mixtures thereof. Preferably, for such a sample, the method is carried out under conditions effective to remove substantially all the dye-labeled terminators from the biological sample mixture.

When the biological sample mixture is a PCR reaction mixture, the small negatively charged molecules are typically selected from the group consisting of primers, degraded dye molecules, deoxynucleotide triphosphates, and mixtures thereof. Preferably, for such a sample, the method is carried out under conditions effective to remove substantially all the primers from the biological sample mixture.

The present invention also provides devices that can be used to carry out methods of the present invention. Such devices include analytical receptacles, such as microfluidic devices and multi-well plates such as microtiter plates, for example.

In one embodiment, a device includes: a plurality of process arrays that include: a plurality of process chambers, each of the process chambers defining a volume for containing a biological sample mixture; and at least one distribution channel connecting the plurality of process chambers; a surface within at least one of the process arrays that includes an anion exchange material (preferably, quaternary ammonium ions). Preferably, the device further includes a plurality of valves, wherein at least one of the valves is located along the at least one distribution channel. Preferably, in the device, the surface that includes an anion exchange material also includes an anion exchange material partially coated with a negatively charged polymer (preferably, a polyelectrolyte). Preferably, the anion exchange material and/or the negatively charged polymer are pattern coated.

In yet another embodiment of the device, the present invention provides an analytical receptacle that includes one or more reservoirs and a surface with a cover film adhered to the surface and enclosing the one or more reservoirs; wherein the cover film includes a backing and an adhesive disposed on at least one major surface of the backing and in contact with the receptacle surface; wherein at least a portion of the adhesive has an anion exchange material (preferably, quaternary ammonium ions) disposed thereon. Preferably, the anion exchange material is partially coated with a negatively charged polymer (preferably, a polyelectrolyte). Preferably, the anion exchange material and/or the polymer are pattern coated.

In still another embodiment, there is provided an analytical receptacle that includes a plurality of reservoirs adapted for receipt of a biological sample mixture, wherein at least one reservoir includes a surface that includes an anion exchange material (preferably, quaternary ammonium ions) partially coated with a negatively charged polymer (preferably, a polyelectrolyte) disposed therein.

In another embodiment, the present invention provides a substrate that includes a functionalized surface on which is disposed an anion exchange material partially coated with a negatively charged polymer, wherein the anion exchange material has associated therewith a polyoxyalkylene.

These and other features and advantages of the methods of the invention are described below with respect to illustrative embodiments of the invention.

DETAILED DESCRIPTION OF PREFERRED EMBODIMENTS

Figure 1:
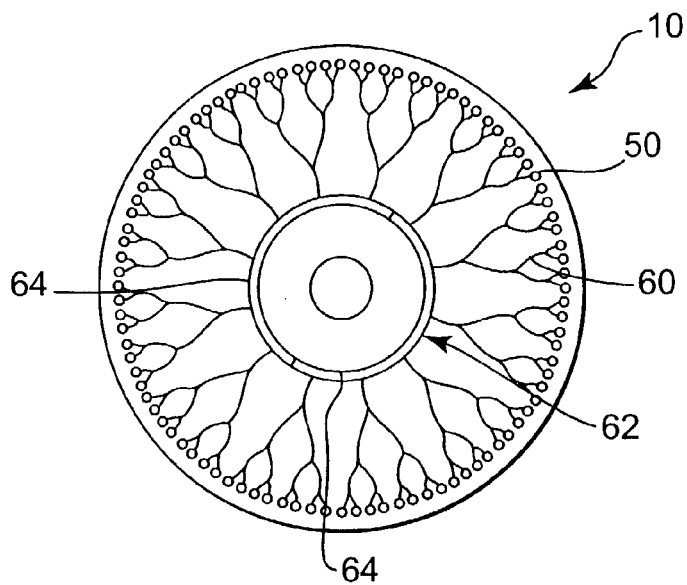
FIG. 1 is a top plan view of one device that can be used in connection with the present invention.

The methods of the present invention utilize solid-phase extraction techniques for processing biological sample mixtures to remove at least a portion of small organic molecules (e.g., molecules having a molecular weight of less than about 6,000) included in such mixtures. These small molecules are typically negatively charged and the solid-phase extraction material is typically an anion exchange material.

For each of the embodiments described herein, the anion exchange material includes (i.e., has associated therewith) a polyoxyalkylene. By this it is meant that an anion exchange material and a polyoxyalkylene are associated physically in some way. For example, they can be mixed together (e.g., before coating), or an anion exchange material can be disposed on (e.g., coated on or bonded to) a support (e.g., a substrate with a functionalized surface) and overcoated with a polyoxyalkylene, or a polyoxyalkylene can be disposed on a support and overcoated with an anion exchange material.

The anion exchange material and polyoxyalkylene construction, in any of these arrangements, is partially overcoated with a negatively charged polymer. For example, if the anion exchange material is overcoated with the polyoxyalkylene, the polyoxyalkylene is partially overcoated with the negatively charged polymer. If the polyoxyalkylene is overcoated with the anion exchange material, the anion exchange material is partially overcoated with the negatively charged polymer.

The biological sample mixture (i.e., a sample containing a biological material such as peptide- and/or nucleotide-containing material) is preferably a biological reaction mixture (e.g., a PCR or cycle sequencing or other nucleic acid amplification reaction mixture). The small organic molecules are preferably residual or unincorporated materials (including degradation products) in biological reactions (e.g., dyes, primers, probes, dNTPs, dye terminators such as ddNTPs, ddNDPs, ddNMPs, and nucleosides). Significantly, using the solid-phase extraction materials of the present invention, the undesirable molecules preferably preferentially adhere to the solid-phase material and the desirable products remain in the biological sample solution.

Examples of nucleic acid amplification reaction mixtures suitable for use in the present invention include, but are not limited to: a) polymerase chain reaction (PCR); b) target polynucleotide amplification methods such as self-sustained sequence replication (3SR) and strand-displacement amplification (SDA); c) methods based on amplification of a signal attached to the target polynucleotide, such as branched chain DNA amplification; d) methods based on amplification of probe DNA, such as ligase chain reaction (LCR) and QB replicase amplification (QBR); e) transcription-based methods, such as ligation activated transcription (LAT) and nucleic acid sequence-based amplification (NASBA); f) cycle sequencing reactions such as Sanger sequencing; and g) various other amplification methods, such as repair chain reaction (RCR) and cycling probe reaction (CPR).

Such methods are particularly desirable for use in the clean-up of PCR reaction mixtures, nucleic acid sequencing reaction mixtures, nucleic acid labeling reaction mixtures, or hybridization reaction mixtures, particularly PCR, nucleic acid sequencing, and nucleic acid labeling reaction mixtures, and more particularly PCR or nucleic acid cycle sequencing or other nucleic acid amplification reaction mixtures. That is, the methods of the present invention are particularly desirable for removing residual reactants and degradation products thereof (e.g., undesirable dye-containing molecules such as ddNDPs and the like) from the desired nucleic acid amplification reaction products (e.g., PCR or sequencing reaction products). The removal of residual dyes (including near-IR, fluorescent, chemiluminescent, UV, and visible) or undesirable dye-containing molecules and other small organic molecules may be important in numerous other genomics and proteomics applications as well (e.g., ligation reactions and protein or peptide affinity binding reactions).

These methods are based on solid-phase extraction techniques, and can be desirably incorporated into high throughput, low volume, integrated microfluidic devices, particularly those being developed for PCR and DNA sequencing. Some desirable qualities of a solid-phase extraction method for PCR or DNA sequencing reaction clean-up for use in an integrated microfluidic device include, for example: 1) the use of high surface area to bed volume ratio porous or nonporous materials that can be incorporated into a spin column, titer well plate, or a well or channel within a flow-through microfluidic device; 2) the use of non-hydrogel based materials that do not require hydration/swelling and are not prone to cracking upon dehydration; 3) no need for specially designed primers or multi-step binding/rinsing/elution protocols; 4) no volatile or corrosive solvents; 5) no leachables that could contaminate DNA products or compromise the structure of the device; and 6) the ability to remove dyes and other residual reactants while not removing a significant amount of PCR or sequencing reaction products.

The methods of the present invention use anion exchange materials effective for selective removal of negatively charged small molecules (e.g., molecules having a molecular weight less than about 6,000, such as dye terminators), while retaining the larger product molecules (e.g., sequencing ladders), which are often negatively charged as well. Herein, "small organic molecules" refer to molecules in a biological sample mixture, such as a PCR or sequencing reaction mixture or other nucleic acid amplification reaction mixture, that are not the desired product molecules. Typically, the small organic molecules that are removed from biological sample mixtures are smaller than the desired products. Preferably, the small organic molecules that are removed from biological sample mixtures have a molecular weight of less than about 6,000. Such small molecules tend to adhere (i.e., adsorb, absorb, or otherwise bind) to the solid-phase extraction materials of the present invention, whereas molecules with a molecular weight of greater than about 8,000 generally do not. For molecules of intermediate molecular weight, the smaller the molecule, the greater the tendency to adhere (i.e., adsorb, absorb, or otherwise bind), whereas the larger the molecule, the less the tendency to adhere (i.e., adsorb, absorb, or otherwise bind). Typically, the desired PCR amplicons have greater than about 50 base pairs and molecular weights of greater than about 33,000. Typically, the desired sequencing ladders have greater than about 18 bases and molecular weights of greater than about 6,000.

Preferably, the anion exchange materials include a surface having bound quaternized nitrogen-containing groups such as quaternary ammonium ions. These quaternary ammonium ions, for example, are typically charge balanced with chloride ions, although other anions can be used for charge balancing and exchange such as iodide, fluoride, nitrate, bisulfite, cyanide, bicarbonate, hydroxide, sulfate, and other small inorganic anions. It may be beneficial, in some cases, to use large organic anions as well as polymeric anions that have low mobilities during electrophoresis in place of small inorganic anions as counter-ions in the anion exchange materials. Such organic/polymeric anions when expelled into solution through the process of ion-exchange may not get preferentially injected into the sequencer, and hence, could result in higher signal strengths of DNA, for example. The concentration of such ions can be tailored for the desired result. For example, for certain methods described herein, the anion exchange materials preferably include at least about 0.01 micromole active groups (e.g., quaternary ammonium ions measured as the amount of chloride) per 1735 $mm^2$ surface area, more preferably, at least about 10 micromoles active groups per 1735 $mm^2$ surface area, and even more preferably, at least about 20 micromoles active groups, per 1735 $mm^2$ surface area, prior to further treatment (e.g., passivation). There is no upper limit to the number of active groups on an anion exchange material for the present invention. This is typically controlled by what is commercially available. Typically, they include no more than about 1000 micromoles active groups (e.g., quaternary ammonium ions measured as the amount of chloride) per 1735 $mm^2$ surface area, and more often, no more than about 200 micromoles active groups per 1735 $mm^2$ surface area, prior to further treatment (e.g., passivation).

Although the anion exchange material preferably includes quaternary ammonium ions, other positively charged ions can be used, particularly those including quaternized nitrogen atoms. Preferred materials include strong anion exchangers having a fixed positive charge (i.e., the ions are positively charged regardless of pH, and particularly at a pH of 8-9). These include, for example, quaternary ammonium anion exchangers (such as those commercially available under the trade designation AMBERLITE, Type I, from Supelco, Bellefonte Pa.), quaternary alkylamine anion exchangers (such as those commercially available under the trade designation DIAION, Type I, from Supelco), trimethylbenzyl ammonium anion exchangers (such as those commercially available under the trade designation DOWEX, Type I, from Supelco), dimethylethanolamine anion exchangers (such as those commercially available under the trade designation AMBERLITE, Type II, from Supelco), quaternary alkylalkanolamine anion exchangers (such as those commercially available under the trade designation DIAION, Type II, from Supelco), and dimethylethanolbezyl ammonium anion exchangers (such as those commercially available under the trade designation DOWEX, Type II, from Supelco). Furthermore, weak anion exchangers could also be used in the present invention if there are a significant number of positively charged species under conditions of use (e.g., at less than pH 7). These include polyamines (such as those commercially available under the trade designations AMBERLITE, DOWEX, and DUOLITE from Supelco) and alkylamines (such as those commercially available under the trade designation DIAION).

A variety of solid-phase extraction materials, preferably including quaternary ammonium groups, are commercially available. In addition to those listed above, suitable commercially available materials include, for example, ion exchange microporous membranes. One such commercially available membrane is available under the trade designation SB-6407 from Pall Corp., East Hills, N.Y., which is a strongly basic positively charged polyethersulfone (PES)/copolymer membrane treated to have ion-exchange capacity on the outer surfaces. The ion-exchange capacity is provided by quaternary ammonium active sites. Such a filter is supplied in the chloride ion form, and has a pore size of about 0.45 micrometer (i.e., micron or μ or μm), a thickness of about 150 micrometers, and an ion exchange capacity of about 20 microequivalents per 3470 square millimeter ($mm^2$) surface area, prior to further treatment (e.g., passivation).

Suitable solid-phase extraction materials can be prepared using a variety of techniques. For example, quaternary ammonium groups can be covalently attached to an underlying substrate (e.g., even as thin as a monolayer), using, for example, a quaternary ammonium functionalized material such as a silane. Alternatively, an amine-containing polymer, such as a polyalkylene imine (e.g., polyethylene imine), can be treated with a quaternizing agent, such as methyl iodide, to form quaternary ammonium ion groups on an underlying substrate. If desired, the polyalkylene imine can be crosslinked prior to quaternization.

In yet another approach, a water-soluble or water-insoluble polyquat (i.e., a polymer containing quaternary ammonium ion groups) can be coated on a substrate with or without subsequent crosslinking. Suitable water-soluble polymers include poly(diallyldimethylammonium chloride), poly(2-hydroxy-3-methacryloxypropyl trimethylammonium chloride), and poly(butylacrylate-methacryloxyethyl trimethylammonium bromide), for example. Suitable water-insoluble polymers include quaternary acrylic copolymers such as those commercially available under the trade designations SYNTRAN Hx31-65 (trimethyl aminoethyl methacrylate/methyl methacrylate) and SYNTRAN Hx31-44 (1-methoxy-2-propanol acrylate copolymer) from Interpolymer Corp., Canton, Mass. Further examples of these materials (and their methods of use) may be found in U.S. patent application Ser. No. 10/027,222 filed on Dec. 20, 2001, and entitled METHODS AND DEVICES FOR REMOVAL OF ORGANIC MOLECULES FROM BIOLOGICAL MIXTURES USING ANION EXCHANGE.

The anion exchange material can be crosslinked if desired, particularly if it is water soluble. For example, crosslinking methods that could be used to crosslink the anion exchange material, or precursors thereof, include the application of heat, ultraviolet (uv) of electron-beam (e-beam) radiation, or chemical methods. For example, a polyquat can be crosslinked by using a heat activated chemical crosslinker such as polyfunctional glycidyl ether (e.g., phenyl glycidyl ether, butyl glycidyl ether) in concentrations from about 0.05 wt-% to about 1.00 wt-%. In some cases, it may be useful to polymerize acrylate monomers functionalized with quaternary ammonium groups, for example, in-situ using uv radiation or e-beam radiation. Standard methods using a uv photoiniator such as IRGACURE 2959 (Ciba Specialty Chemicals, Tarrytown, N.Y.) can be used to polymerize the acrylate-quaternary ammonium monomer. Alternatively, passivation methods can render the water-soluble materials water insoluble (e.g., by precipitation).

Anion exchange materials of the present invention include (i.e., have associated therewith) a polyoxyalkylene (also known as a polyether). The polyoxyalkylene may contain a nucleophilic group such as a primary amine or thiol attached to the terminus of the polyether backbone, thus resulting in a nucleophilic polyoxyalkylene. Examples of suitable polyoxyalkylenes include, but are not limited to, polyoxyethylene, polyoxypropylene, polyoxyethylenediamine, polyoxypropylenediamine, polyoxyethyleneamine, polyoxypropylenetriamine, polyoxyethylenethiol, polyoxypropylenethiol, and combinations thereof. Nucleophilic polyoxyalkylenes are preferred because they can form crosslinked networks if desired. Preferred nucleophilic polyoxyalkylenes include polyoxyalkylenediamines or poly (alkylene glycol diamines), such as polyoxyethylenediamine and polyoxypropylenediamine.

A polyoxyalkylene is incorporated into an anion exchange material in an amount effective to remove residual or unincorporated materials (including degradation products) in biological reactions (e.g., dyes, primers, probes, dNTPs, dye terminators such as ddNTPs, ddNDPs, ddNMPs, and nucleosides). Alternatively, a nucleophilic polyoxyalkylene is incorporated into an anion exchange material in an amount effective to form a crosslinked network. Preferably, at least about 0.0005 micromole of polyoxyalkylene (preferably, a nucleophilic polyoxyalkylene) is incorporated per 1735 $cm^2$ of an anion exchange material (typically, a coated anion exchange material). Preferably, no greater than about 10 micromoles of polyoxyalkylene (preferably, a nucleophilic polyoxyalkylene) is incorporated per 1735 $cm^2$ of an anion exchange material (typically, a coated anion exchange material).

Polyoxyalkylenes can be introduced into the anion-exchange material in a variety of ways. When a commercial functionalized membrane, such as the anion-exchange material available under the trade designation of SB-6407 from the Pall Corporation, East Hills, N.Y., is used, the polyoxyalkylene can be introduced by dip-coating the membrane in a dilute (e.g., about 0.05 wt-% to about 3.00 wt-%) aqueous or alcoholic (e.g., 1-methoxy-2-propanol) solution of polyoxyalkylene.

Alternatively, a substrate (e.g., a polymer substrate) in the form of a porous/non-porous film, foam, frit, or a membrane, for example, can be functionalized using an amine-reactive or a thiol-reactive material, for example, prior to incorporating the anion exchange material and the polyoxyalkylene. Preferably, the substrate is functionalized by first coating, for example, an azlactone polymer (e.g., dimethyl acrylamide and vinyl dimethyl azlactone crosslinked with ethylene diamine) onto a substrate. This can be done, for example, using approximately 5 grams of a 1 percent by weight (wt-%) solution of crosslinked azlactone in isopropyl alcohol to apply a coating weight of about 0.5 grams per square meter ($g/m^2$). Azlactone is preferred in that it contains amine-reactive functionalities which provide for rapid coupling. Amine reactive or thiol reactive silanes can be used in place of the azlactone. A layer of an anion exchange material (such as that available under the trade designation SYNTRAN Hx31-65 from Interpolymer Corp., Canton, Mass.) can be deposited on the azlactone layer, as described in U.S. patent application Ser. No. 10/027,222 filed on Dec. 20, 2001, and entitled METHODS AND DEVICES FOR REMOVAL OF ORGANIC MOLECULES FROM BIOLOGICAL MIXTURES USING ANION EXCHANGE, followed by a coating of a polyoxyalkylene.

In yet another embodiment, the anion exchange material and the polyoxyalkylene can be mixed together and coated on the azlactone functionalized polymer substrate.

Nucleophilic polyoxyalkylenes can be optionally crosslinked using an appropriate crosslinker such as an aliphatic triglycidyl ether available under the trade designation HELOXY Modifier 48 from Resolution Performance Products, Houston, Tex., for example. Typical crosslinker concentrations range from about 0.05 wt-% to about 1.00 wt-%.

If desired, the anion exchange materials can also include other additives such as plasticizers to enhance the flexibility of films formed therefrom. Examples include gelatin and dibutyl phthalate.

Anion exchange materials (e.g., surfaces with bound quaternary ammonium ion groups) without further treatment (e.g., passivation) can be used in separation methods of the present invention, although they are generally nonselective. That is, they will remove the desired product (e.g., DNA sequencing ladders) as well as the undesired small molecules (e.g., dye terminators). If the concentration of the desired product is sufficiently large in a sample mixture, although the recovery would be quite low, it may be suitable for certain applications.

Preferably and advantageously, however, the anion exchange materials (e.g., bound quaternary ammonium ions) are partially coated with a negatively charged polymer, preferably a negatively charged polyelectrolyte. This partial passivation of the positive charges of the anion exchange material (e.g., quaternary ammonium ion groups) by the negatively charged polymer results in the remaining positively charged sites to be available for binding of small molecules through exchange with the counterions (typically with chloride ions). As a result, the surface is more selective, which provides better recovery as well as reproducibility. Significantly, passivation can also render water-soluble anion exchange materials suitable for use with aqueous sample mixtures, for example, by anion exchange and precipitation.

Suitable negatively charged polymers include those with multiple charges per molecule or with one or more charged end groups. For example, the negatively charged polymer can be a polyalkylene oxide (preferably, polyethylene oxide, polypropylene oxide, polyethylene-propylene oxide) with a negatively charged end group such as a carboxylate, as well as silanes and polyethylene glycol silanes functionalized with a negatively charged end group.

Preferred negatively charged polymers are molecules, typically macromolecules, in which a substantial portion of the constitutional units carry a charge when dissolved in an ionizing solvent. Suitable negatively charged polyelectrolytes are those that typically have molecular weights above 10,000, and preferably have low non-specific binding to components in a biological mixture. Suitable examples include a polystryene sulfonic acid (e.g., poly(sodium 4-styrenesulfonate) or PSSA), polyvinyl phosphonic acid, polyvinyl boric acid, polyvinyl sulfonic acid, polyvinyl sulfuric acid, polystyrene phosphonic acid, polyacrylic acid, polymethacrylic acid, lignosulfonate, carrageenan, heparin, chondritin sulfate, and salts or other derivatives thereof. Various combinations of these can be used if desired.

The negatively charged polymer (e.g., polyelectrolyte) is present on the anion exchange material such that it only partially (i.e., not completely) blocks the positively charged species. Preferably, it is present in an amount of at least about 0.015 microgram (µg), and more preferably, at least about 0.03 milligram (mg), per 1735 mm² surface area. The upper limit to the amount of negatively charged polymer is dependent on the number of active groups in the anion exchange material. Generally, there is no upper limit as long as all the active anion exchange groups are not blocked by the polymer, i.e., are still available for binding of small molecules. Typically, a polymer is present on the anion exchange material in an amount of no greater than about 5 mg per 1735 mm² surface area, and more often, no greater than about 1 mg per 1735 mm² surface area, although it could be much higher (e.g., 100 mg per 1735 mm² surface area).

The negatively charged polymer is typically applied as an aqueous solution to the anion exchange material (e.g., surface having bound quaternary ammonium ion groups thereon). The preferred challenge concentration (i.e., the concentration of the solution) of the negatively charged polymer is chosen to provide maximum recovery of the desired product (e.g., DNA), preferably with substantially complete removal of dye-containing small organic molecules. Typically, it has been found that a challenge concentration of at least about 0.0001 percent by weight (wt-%) in deionized water (for a sample of material being coated having about 434 mm² surface area) provides suitable recovery values. Increasing recovery generally occurs with higher challenge concentrations; however, when the challenge concentration exceeds a threshold value (e.g., 1.0 wt-% for a sample of material being coated having about 434 mm² surface area), dye-containing small organic molecules can be incompletely removed. Although this results in good signal intensity, poor quality of sequencing chromatograms, for example, can occur.

In addition to improving product (e.g., DNA) recovery, passivation with the negatively charged polymer can alter the time taken for sample processing (e.g., PCR or sequencing reaction mixture clean-up). For example, in the case of commercially available PES membranes, higher challenge concentrations (e.g., higher than about 0.03 wt-% for a sample being coated having about 434 mm² surface area) of a polymer such as a polyelectrolyte can result in longer times for substantially complete removal of dye-containing small organic molecules. Relatively long processing (e.g., clean-up) times (e.g., about 10-15 minutes) can be useful for manual processing of many sample mixtures; however, in a microfluidic device, it is advantageous to reduce processing times. Thus, lower challenge concentrations (e.g., no greater than about 0.005 wt-% for a sample being coated having about 434 mm² surface area) of a polymer such as a polyelectrolyte are preferred for such applications.

The anion exchange material (e.g., material containing quaternary ammonium ion groups) and particularly the anion exchange material partially coated with a negatively charged polymer (e.g., a polyelectrolyte) (all of which are referred to herein as the "active chemistry") can be applied to the surfaces of a variety of substrates. Suitable substrates include beads, membranes, adhesive-coated articles, frits, foams, gels, microreplicated articles, or on the walls of a channel/well of an analytical receptacle. Substrates with higher surface areas enhance contact area, which can improve processing efficiency. The substrate can be treated for improved adhesion/surface area by a variety of treatments such as oxygen plasma, diamond-like glass deposition, corona treatment, e-beam or uv radiation, heat, as well as other similar techniques.

Such substrates can be porous and nonporous; however, porous materials have the advantage of large surface area to bed volume ratios and are particularly useful in flow-through applications. Suitable materials include high surface area organic and inorganic materials, which are routinely used in adsorption chromatography for decolorizing synthetic reactions.

Inorganic materials include, for example, silica gel, alumina, zirconia, and diatomaceous earth. Molecular sieves, such as zeolites (i.e., sodium and calcium aluminosilicates), can also be used in a similar fashion. Zeolites have the additional advantage that they can selectively trap small ionic species within their pores based on size. Porous ceramic particles and membranes (alumina, zirconia, silica, and aluminosilicate) can also be used.

Organic materials include, for example, oligosaccharides, polyesters, polysulfones, polycarbonates, polyvinyl chlorides, polyvinyl acetates, polymethyl methacrylates, cellulose esters, polyesters, and the like. Many other organic materials can be used, which are typically available in the form of membranes, films, or particles.

The anion exchange materials, particularly when partially coated with a negatively charged polymer (e.g., a polyelectrolyte), provide sites for relatively strong binding of the undesirable small organic molecules (e.g., dye terminators) while repelling larger negatively charged product molecules (e.g., DNA sequencing ladders) based on charge and size effects, thereby allowing for selective clean-up.

The anion exchange materials, preferably the polymer-coated anion exchange materials, can be used effectively for purification of nucleic acid amplicons after the polymerase chain reaction (PCR), for example. As is well known, PCR allows for analysis of extremely small amounts of nucleic acid (e.g., DNA). Briefly, a nucleic acid molecule (e.g., DNA template) is repeatedly synthesized using a polymerase enzyme (such as Taq DNA polymerase), an excess of two oligonucleotide primers (capable of flanking the region to be amplified and acting as a point of initiation of synthesis when placed under conditions in which synthesis of a primer extension product that is complementary to a target nucleic acid strand is induced), and free deoxynucleotide triphosphates (dNTPs, e.g., dGTP, dATP, dCTP and dTTP), which results in the amplification of a particular sequence by a millionfold or more. The resultant extension or amplification products are typically referred to as "PCR products" or "PCR amplicons."

Preferably, the PCR products incorporate a detectable label or tag, as can other materials in the PCR reaction mixture (e.g., primers and dNTPs). Thus, PCR amplification of target nucleic acid is preferably accomplished by utilizing at least one primer containing a detectable tag. For example, ultraviolet, visible, or infrared absorbing tags could be used that would produce specific ultraviolet, visible, or infrared signals. Examples of a wide variety of tags (a chemical moiety that is used to uniquely identify a nucleic acid of interest) are disclosed in International Publication No. WO 97/27325. Particularly preferred such tags are fluorescent or chemiluminescent agents. These are typically dye compounds that emit visible radiation in passing from a higher to a lower electronic state, typically in which the time interval between adsorption and emission of energy is relatively short, generally on the order of about $10^{-8}$ to about $10^{-3}$ second. Suitable fluorescent or chemiluminescent compounds can include fluorescein, rhodamine, luciferin, as well as a wide variety of others known to one of skill in the art.

In clean-up of PCR reaction mixtures after PCR has occurred, the undesired negatively charged small molecules include residual primers (labeled or unlabeled), degraded dye molecules (i.e., dye molecules or fragments thereof severed from the dye-labeled primers), and dNTPs (labeled or unlabeled). Of these molecules it is particularly important to remove the primers.

Preferably, using the methods of the present invention at least a portion of one or more of these unincorporated materials can be separated from the PCR products (i.e., removed from the PCR reaction mixture). Typically, the smaller molecules are removed (e.g., dNTPs) more easily than the larger molecules (primers). More preferably, at least about 90% of the residual primers and/or at least about 70% of the dNTPs are removed from a PCR reaction mixture using the methods of the present invention. Even more preferably, substantially all (i.e., at least about 95%) of one or more of the residual primers, degraded dye molecules, and dNTPs, are separated from the desired PCR products. Most preferably, substantially all (i.e., at least about 95%) of all the residual primers, degraded dye molecules, and dNTPs, are separated from the desired PCR products. The level of removal of primers can be determined by the OLIGREEN ssDNA quantitation reagent (Molecular Probes, Eugene, Oreg.), high pressure liquid chromatography (HPLC), and capillary electrophoresis (CE). The level of removal of dNTPs can be determined by absorbance at 1260 nm, HPLC, and CE.

Preferably, using the methods of the present invention, at least about 30% of the desired PCR product (e.g., DNA amplicon) is recovered from a PCR reaction mixture. More preferably, at least about 50% of the desired PCR product is recovered from a PCR reaction mixture. Even more preferably, at least about 70% of the desired PCR product is recovered from a PCR reaction mixture. Most preferably, at least about 90% of the desired PCR product is recovered from a PCR reaction mixture. The level of PCR product recovery can be determined by Agilent 2100 Bioanalyzer available from Agilent Technologies, Palo Alto, Calif.

For certain methods of PCR reaction mixture clean-up, the anion exchange materials preferably include at least about 10 micromoles, and often up to about 200 micromoles, active groups (e.g., quaternary ammonium ions measured as the amount of chloride) per 1735 mm$^2$ surface area, prior to further treatment (e.g., passivation). The passivation level (i.e., the level of negatively charged polymer (e.g., polyelectrolyte)) is generally at least about 0.03 mg, and often up to about 30 mg, per 1735 mm$^2$ surface area and typically no greater than 5 mg per 1735 mm$^2$. Challenge concentration of the passivating polymer is typically 2-3 times higher for PCR than for sequencing. The clean-up is preferably carried out at room temperature, although higher temperatures could be used if desired. A typical time for clean-up is less than about 5 minutes.

These anion exchange materials, preferably the polymer-coated anion exchange materials, can also be used effectively for purification of nucleic acid (e.g., DNA) sequencing ladders after, for example, Sanger cycling. As is well known, sequencing, such as Sanger sequencing, produces a nested set of fragments from a template strand (e.g., a DNA template) by replicating the template strand to be sequenced. Briefly, a nucleic acid molecule (e.g., DNA template) of unknown sequence is combined with a nucleic acid polymerase, a primer, free deoxynucleotide triphosphates (dNTPs, e.g., dGTP, dATP, dCTP and dTTP), and one of the four free dideoxynucleotide triphosphates (a dideoxynucleotide cannot bond to other nucleotides because its 3' end is modified, thus, when dideoxynucleotides are incorporated, strand synthesis stops) to produce a random sample of varying length segments of nucleic acid. Thus, sequencing mixtures contain salts, enzymes, unincorporated deoxynucleotide triphosphates (dNTPs), template nucleic acid, primers, and the resultant nucleic acid sequencing ladders. Various of these materials (e.g., primers and dNTPs) can be labeled with dye molecules or unlabeled. Such mixtures also include unincorporated dye-labeled dideoxynucleotide terminators such as dye-labeled dideoxynucleotide triphosphates (ddNTPs), which can be hydrolyzed (e.g., treated enzymatically with a phosphatase such as shrimp alkaline phosphatase to dephosphorylate residual nucleotide triphosphates) to form dye-labeled artifacts such as dye-labeled dideoxynucleotide diphosphates (ddNDPs), dye-labeled dideoxynucleotide monophosphates (ddNMPs), and dye-labeled dideoxynucleosides. As described in International Publication No. WO 01/25490, such unincorporated dye-labeled terminators typically have to be removed from the DNA sequencing ladders prior to electrophoresis. Herein, the "dye-labeled terminators" are also referred to as "dye terminators" and include ddNTPs, ddNDPs, ddNMPs, and dideoxynucleosides. Particularly preferred such dyes are fluorescent or chemiluminescent agents and include fluorescein, rhodamine, luciferin, etc.

In clean-up of sequencing reaction mixtures after cycling has occurred, the undesired negatively charged small molecules include residual primers (labeled or unlabeled), degraded dye molecules (i.e., dye molecules or fragments thereof severed from the dye-labeled terminators), dNTPs (labeled or unlabeled), and dye terminators. Of these, it is particularly important to remove the dye terminators. Preferably, using the methods of the present invention at least a portion of one or more of these unincorporated materials can be separated from the sequencing products (i.e., removed from the sequencing reaction mixture). Typically, the smaller molecules are removed (e.g., dNTPs) more easily than the larger molecules (primers) and the more highly charged molecules are removed more easily than the less highly charged molecules (e.g., the ease of removal decreases from ddNTPs to ddNDPs to ddNMPs to nucleosides). More preferably, substantially all (i.e., at least about 95%) of one or more of the residual primers, degraded dye molecules, dNTPs, and dye terminators are separated from the sequencing products. Most preferably, substantially all (at least about 95%) of all the residual primers, degraded dye molecules, dNTPs, and ddNTPs are separated from the sequencing products. Significantly and preferably, using the methods of the present invention, at least about 95%, more preferably, at least about 98%, and most preferably, 100%, of all the dye terminators are separated from sequencing products. Such products can then be analyzed by sequencing. The level of removal of dye terminators can be determined by fluorescence, CE, or HPLC.

Preferably, using the methods of the present invention, at least about 30% of the desired sequencing product (e.g., DNA ladder) is recovered from a cycle sequencing reaction mixture. More preferably, at least about 50% of the desired sequencing product is recovered from a cycle sequencing reaction mixture. Even more preferably, at least about 70% of the desired sequencing product is recovered from a cycle sequencing reaction mixture. Most preferably, at least about 90% of the desired sequencing product is recovered from a cycle sequencing reaction mixture. The level of product recovery can be determined by CE, for example.

For certain methods of sequencing reaction mixture clean-up, the anion exchange materials preferably include at least about 10 micromoles, and often up to about 200 micromoles, active groups (e.g., quaternary ammonium ions measured as the amount of chloride) per 1735 mm$^2$ surface area, prior to further treatment (e.g., passivation). The passivation level (i.e., the level of negatively charged polymer (e.g., polyelectrolyte)) is generally about 0.03 mg, and often up to about 30 mg, per 1735 mm$^2$ surface area and typically no greater than 5 mg per 1735 mm$^2$. The clean-up is preferably carried out at room temperature, although higher temperatures could be used if desired. A typical time for clean-up is less than about 5 minutes.

The active chemistry, particularly the polymer-coated anion exchange materials (e.g., the partially coated quaternary ammonium ion groups), can be incorporated into flow-through devices or non-flow-through formats. If a non-flow-through format is used, the reaction mixture can be incubated with or without mixing, preferably with mixing, for a given period of time and the resultant supernatant containing at least partially purified product (e.g., DNA amplicons) can be removed and analyzed.

Diffusion of small molecules to a surface having the active chemistry thereon can be improved by providing adequate mixing of the reactants. This can be accomplished by vortexing, shaking, heating, sonicating, etc. Providing intimate mixing can result in shorter times for processing (e.g., clean-up), better product recovery levels, and/or better reproducibility.

The active chemistry described herein, particularly the polymer coated anion exchange materials (e.g., the partially coated quaternary ammonium ion groups), can be incorporated into a variety of devices, particularly analytical receptacles. As used herein, analytical receptacles are devices that receive a sample, reagent, or solvent into one or more reservoirs, which may or may not designed for filtration. Examples include assay plate arrays (e.g., multi-well plates such as microtiter plates), discrete or continuous (e.g., strip or tape) structures containing a plurality of wells, channels, or other reservoirs, and arrays of the type used in 96-well filter plate assemblies (e.g., of the type described in U.S. Pat. No. 5,620,663 (Aysta et al.)).

Preferred analytical receptacles, without further modification, provide an open system of one or more reservoirs (e.g., wells or channels) to which fluids may be added directly. A cover film is typically applied along the length and width of an analytical receptacle to seal the receptacle, preferably the reservoir(s) of the receptacle, and create a closed system. Preferably, this results in producing individually sealed enclosures, which can be substantially continuous or discrete (i.e., discontinuous) structures.

A cover film, which acts as a sealing membrane, can include an adhesive, preferably, a pressure sensitive adhesive, disposed on a backing (preferably, a transparent backing). The adhesive is selected such that it adheres well to materials of which conventional analytical receptacles are made (preferably polyolefins, polystyrene, polycarbonate, or combinations thereof), maintains adhesion during high and low temperature storage (e.g., about −80° C. to about 200° C.) while providing an effective seal against sample evaporation, and does not substantially dissolve in or otherwise react with the components of the biological sample mixture. Thus, the type of adhesive is not critical as long as it does not interfere (e.g., bind DNA, dissolve, etc.) with the removal of unwanted materials from a biological sample mixture. Preferred adhesives include those typically used on cover films of analytical devices in which biological reactions are carried out. These include poly-alpha olefins and silicones, for example, as described in International Publication Nos. WO 00/45180 and WO 00/68336.

The active chemistry described herein can be incorporated into the analytical receptacle in a variety of ways. For example, it can be coated onto the walls of one or more reservoirs, it can be in the form of a flow-through membrane placed in one or more reservoirs, it can be coated on a film (which can be continuous or discontinuous or in the form of a plurality of pieces) placed in one or more reservoirs, or it can be coated on the adhesive of the adhesive-coated cover film. The active chemistry, either the anion exchange material (e.g., quaternary ammonium ions) or the negatively charged polymer or both, can be pattern coated.

The active chemistry described herein, particularly the polymer-coated anion exchange materials (e.g., the partially coated quaternary ammonium ion groups), is particularly well suited for use in a high throughput microfluidic device resulting in reagent and time savings, as well as elimination of the need to elute in the conventional sense (i.e., washing away the unwanted components from the bound desired products followed by removing the desired products). Such devices typically require low bed volume clean-up media for the purification of small volume reactions. The active chemistry can be incorporated into a microfluidic device in a variety of manners.

In one embodiment, an adhesive-coated cover film (or inner walls) of a microfluidic device can be coated with, preferably pattern coated with, the active chemistry (e.g., a polyquat followed by a PSSA solution). This coating, particularly pattern coating, can be accomplished by a variety of methods such as spray drying, dip coating, brush coating, knife coating, roll coating, ink-jet coating, screen printing, electrostatic deposition, etc. An unpurified biological sample mixture, e.g., a PCR or DNA sequencing reaction mixture, can be spun into a clean-up chamber containing the active chemistry on either or both the top and bottom surfaces of the chamber. The speed of this reaction can be enhanced by ensuring intimate contact of the solution with the chamber walls by mixing, vortexing, shaking, or through compression of the walls (made of a compliant material) of the device, etc. The purified reaction mixture is collected and ready for subsequent analysis (e.g., by injection into a DNA sequencing instrument).

In another embodiment, a solid-phase material having the active chemistry coated thereon can be positioned within a microfluidic compartment or channel. For example, a device having at least one process array that includes two connected process chambers, at least one of the process chambers and/or at least one volume defined by a connection (i.e., distribution channel) between at least two process chambers can include the solid-phase material. In this arrangement, if the solid-phase material is in the form of a porous material, an unpurified biological sample solution, e.g., PCR or DNA sequencing reaction mixture, passes through the solid-phase material, allowing sufficient residence time to trap the undesirable components (e.g., excess unincorporated dye terminators). Alternatively, if the solid-phase material is in the form of a nonporous material, the unpurified biological sample solution passes by the material. The contact area of the sample with the solid-phase material can be enhanced upon selection of a solid-phase material within larger surface area. The purified reaction mixture is collected and ready for subsequent analysis, such as occurs, for example, upon injection into a DNA sequencing instrument.

Although the methods of the present invention can be used in a variety of devices, a variety of illustrative embodiments of some suitable devices may be described in, e.g., U.S. patent application Publication No. US 2002/0047003 A1 published on Apr. 25, 2002 and entitled ENHANCED SAMPLE PROCESSING DEVICES SYSTEMS AND METHODS and U.S. patent application Publication No. 2002/0064885 A1 published on May 30, 2002 and entitled SAMPLE PROCESSING DEVICES; U.S. patent application Publication No. US 2002/0048533 A1 published on Apr. 25, 2002 and entitled SAMPLE PROCESSING DEVICES AND CARRIERS; and U.S. patent application Publication No. US 2002/0001848 A1 published on Jan. 3, 2002 and entitled MULTI-FORMAT SAMPLE PROCESSING DEVICES, METHODS AND SYSTEMS.

The methods described herein can be used in a variety of different processes requiring at least partial removal of dyes or other organic molecules from biological reaction mixtures contained in the process arrays of microfluidic devices. Examples of such processes involve the clean-up of chemical reaction mixtures, e.g., nucleic acid amplification, which may or may not also be carried out in process arrays of the device. Some or all of the required reagents for anion exchange chemistry for clean-up (e.g., a polyquat partially coated with PSSA) may be present in the device as manufactured, they may be loaded into the process arrays after manufacture of the device, they may be loaded in the process arrays just before introduction of the sample, or they may be mixed with sample before loading into the process arrays.

A preferred method involves the use of a device with a plurality of process arrays such as those illustrated in U.S. patent application Publication No. US 2002/0047003 A1 published on Apr. 25, 2002 and entitled ENHANCED SAMPLE PROCESSING DEVICES SYSTEMS AND METHODS. Each of the process arrays includes a number of chambers (e.g., loading chambers and process chambers such as reaction chambers or clean-up chambers) that are preferably arranged generally radially on a device (such that centrifugal forces can move fluids sequentially from chamber to chamber, for example). The chambers within each of the arrays are in fluid communication using channels or other conduits that may, in some embodiments, include valve structures to control the movement as desired.

Using such a device, starting sample material, e.g., lysed blood cells, is provided in a loading chamber. A filter is preferably provided to filter the starting sample material as it moves from the loading chamber to a first process chambers. The first process chambers preferably include suitable PCR primers as supplied, e.g., dried down in each of the chambers. Each of the chambers may include the same primer or different primers depending on the nature of the investigation being performed on the starting sample material. One alternative to providing the primers in the process chambers before loading the sample is to add a suitable primer to the loading chamber with the starting sample material (provided that the primer is capable of passing through the filter, if present).

After locating the starting sample material and any required primers in the process chambers, the materials in the process chambers are thermally cycled under conditions suitable for PCR amplification of the selected genetic material.

After completion of the PCR amplification process, the materials in each of the first process chambers may be moved through another filter chamber (one filter chamber for each process chamber) to remove unwanted materials from the amplified materials, e.g., PCR primers, unwanted materials in the starting sample that were not removed by filter, etc. The filter chambers contain the active chemistry coated on surfaces of the chamber, for example. Alternatively, or additionally, they may contain the solid-phase materials described above for sample clean-up (e.g., dye removal). The area in which the active chemistry is included in such devices can be a chamber or in the volume defined by a connection between two chambers or both.

After clean-up of the sample materials in the filter chambers, the filtered PCR amplification products from each of the first process chambers are moved into second process chambers for, e.g., sequence cycling of the genetic materials amplified in the first process chambers through appropriate control of the thermal conditions encountered in second process chambers.

After completion of the sequence cycling (e.g., Sanger sequencing) process, the materials in each of the second process chambers may be moved through another filter chamber (one filter chamber for each process chamber) to remove unwanted materials from the sequencing ladders (e.g., sequencing primers, ddNTPs, etc.). The filter chambers contain the active chemistry coated on surfaces of the chamber, for example. Alternatively, or additionally, they may contain the solid-phase materials described above for sample clean-up (e.g., dye removal). Again, the active chemistry can be in a chamber or between chambers in a channel.

The present invention also provides devices for processing (e.g., clean-up) of sample mixtures. The sample materials may be located in a plurality of process chambers in the device which, in various aspects, may include one or more of: a reflective layer (e.g., a metallic layer); baffle structures to enhance cooling during rotation of the device; capture plugs to capture filtering materials; valve mechanisms capable of being selectively opened, thermal indicators for monitoring/controlling the temperatures in process chambers, absorptive materials in the process chambers to enhance energy absorption, etc. In various embodiments, the devices may include reagents, filters, and other sample processing materials in the process chambers.

Among the thermal control advantages of the devices of the present invention are chamber-to-chamber temperature uniformity, comparable chamber-to-chamber temperature transition rates, and the increased speed at which thermal energy can be added or removed from the process chambers. Among the device features than can contribute to these thermal control advantages are the inclusion of a reflective layer (e.g., metallic) in the device, baffle structures to assist in removing thermal energy from the device, and low thermal mass of the device. By including thermal indicators in the devices, enhanced control over chamber temperature may be achieved even as the device is rotated during processing.

One illustrative device manufactured according to the principles of the present invention is illustrated in FIG. 1. The device 10 is preferably in the shape of a circular disk as illustrated in FIG. 1, although any other shape than can be rotated could be used in place of the preferred circular disk.

The device includes a plurality of process chambers 50, each of which defines a volume for containing a sample and any other materials that are to be thermally cycled with the sample. The illustrated device 10 includes ninety-six process chambers 50, although it will be understood that the exact number of process chambers provided in connection with a device manufactured according to the present invention may be greater than or less than ninety-six, as desired.

The process chambers 50 in the illustrative device 10 are in the form of wells, although the process chambers in devices of the present invention may be provided in the form of capillaries, passageways, channels, grooves, or any other suitably defined volume. The process chambers 50 are in fluid communication with distribution channels 60 that, together with the common loading chamber 62, provide a distribution system for distributing samples to the process chambers 50. Introduction of samples into the device 10 through the loading chamber 62 may be accomplished by rotating the device 10 about a central axis of rotation such that the sample materials are moved outwardly due to centrifugal forces generated during rotation. Before the device 10 is rotated, the sample can be introduced into the loading chamber 62 for delivery to the process chambers 50 through distribution channels 60.

The process chambers 50 and/or distribution channels 60 may include ports through which air can escape and/or features to assist in distribution of the sample materials to the process chambers 50. Alternatively, it may be possible to provide a closed distribution system, i.e., a system in which materials may be introduced through an opening through which air within the process chambers 50 and/or distribution channels 60 also escapes during the distribution process. In another alternative, sample materials could be loaded into the process chambers 50 under the assistance of vacuum or pressure.

The process chamber 50, associated distribution channels 60, and loading chamber 60 all combine to form a number of process arrays on the device 10, with each process array including one of the process chambers 50, the distribution channels 60 connecting the process chamber 50 to the loading chamber 62, and the loading chamber 62 itself. The process arrays may preferably be arranged radially on the device 10.

Figure 2:
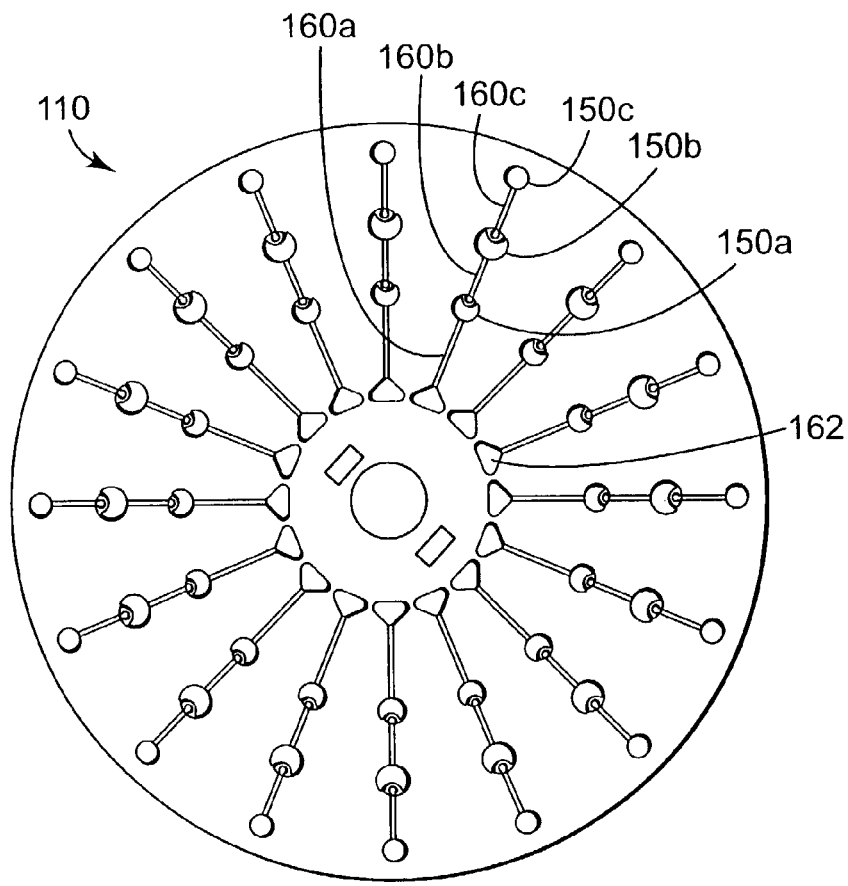
FIG. 2 depicts an alternative device that can be used in connection with the present invention.
Figure 3:
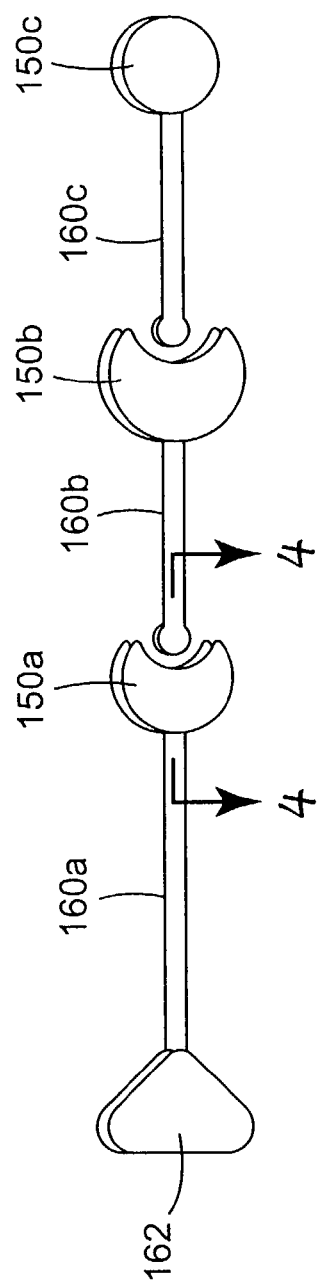
FIG. 3 is an enlarged view of one process array on the device of FIG. 2.
Figure 4:
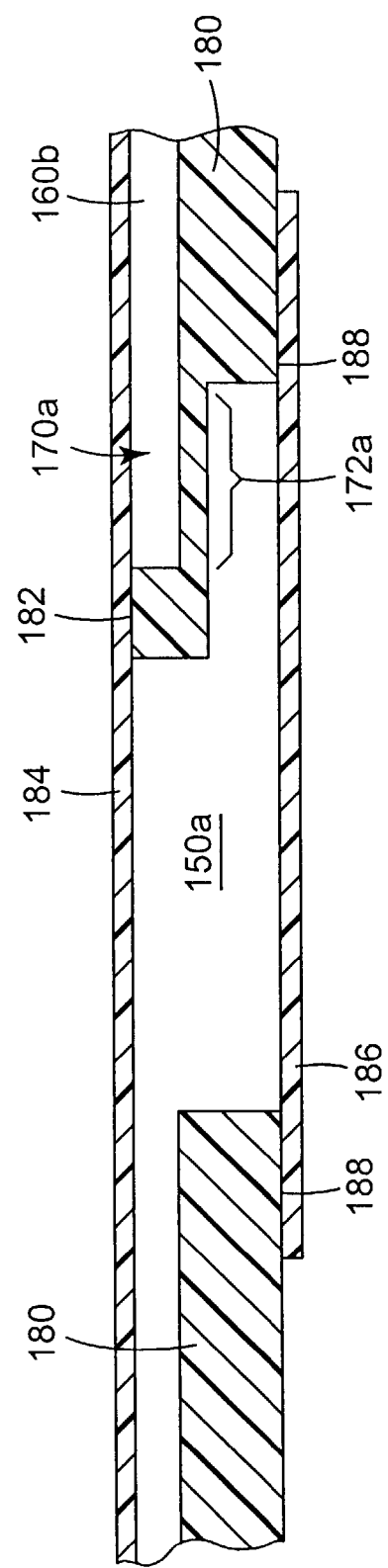
FIG. 4 is a cross-sectional view of a portion of the process array of FIG. 3, taken along line 4-4 in FIG. 3.

Referring to FIGS. 2-4, an alternative device 110 with a different arrangement of process arrays is depicted that can be used in place of the device 10 of FIG. 1. The device 110 seen in FIG. 2 includes a number of independent process arrays, each of which includes distribution channels 160a and 160b connecting a loading chamber 162 and process chambers 150a, 150b and 150c. The process arrays on the device 110 are independent in the sense that the different process arrays are not in fluid communication with each other as are the process arrays on the device 10 of FIG. 1, but are, instead, separate and distinct from each other.

It is preferred that the process arrays be arranged radially from the center of the device 110. As a result, rotation of the device can be used to move sample materials successively through the chambers and distribution channels. The depicted device 110 includes sixteen process arrays, although it will be understood that devices used in connection with the present invention can include any desired number of process arrays. Furthermore, although each of the process arrays of device 110 includes a loading chamber and three process chambers connected sequentially by distribution channels, it should be understood that a process array of the present invention may include as few as two interconnected chambers.

FIG. 3 is an enlarged view of one process array on device 110 and FIG. 4 is a cross-sectional view of a portion of the process array of FIG. 3. Each process array includes a loading chamber 162 connected to a first process chamber 150a through a distribution channel 160a. The first process chamber 150a is, in turn, connected to a second process chamber 150b through a distribution channel 160b. The second process chamber 150b is connected to a third process chamber 150c, that, in the depicted process array, is located furthest from the loading chamber 162. If materials are to be moved within the process array from the loading chamber 162 towards the third process chamber 150c, it may be preferred that the loading chamber 162 be located closer to the axis of rotation of the device than the process chambers 150a, 150b or 150c.

The cross-sectional view of FIG. 4 depicts a number of other features of one potential construction of a device that could be used in connection with the present invention. The construction includes a core 180 in which the features of the device are formed. One surface 182 of the core 180 may include a cover film 184 attached thereto. The cover film 184 may be of any suitable construction, although the adhesive cover films described herein may be preferred.

The bottom of the process chamber 150a also includes a cover 186 attached to the surface 188 of the core 180 to enclose the volume of the process chamber 150a. Like the cover 184, it may be preferred that the cover 186 be attached to and seal with the core 180 using an adhesive, e.g. a pressure sensitive adhesive as described herein. It may be preferred that the cover 186 be provided in the form of a metallic layer that enhances thermal energy transfer into and out of the process chamber 150a. In some embodiments, the cover 186 may be provided in the form of a ring-shaped structure as described in, e.g., U.S. patent application Publication No. US 2002/0047003 A1 published on Apr. 25, 2002 and entitled ENHANCED SAMPLE PROCESSING DEVICES, SYSTEMS AND METHODS.

The first process chamber 150a includes a valve structure in the form of a lip 170a that protrudes into the boundaries of what would otherwise be a generally circular first process chamber 150a. The lip 170a is in the form of an undercut extension into the volume of the process chamber 150a as seen in, e.g., FIG. 4. When an opening is provided in the lip 170a, sample materials in the process chamber 150a can move into the distribution channel 160b for delivery to the second process chamber 150b is desired. In the absence of an opening in the lip 170a, movement of materials into the second process chamber 150b through distribution channel 160b is prevented by the lip 170a which otherwise seals against the cover 184 to prevent the flow of sample materials from the first process chamber 150a into the distribution channel 160b.

The lip 170a may preferably include an area 172a of reduced thickness. This may be seen best in the cross-sectional view of FIG. 4. When the area 172a is, e.g., pierced or otherwise deformed to include an opening formed therethrough, any sample materials located in the volume of the process chamber 150a can move from the chamber into the distribution channel 160b for delivery to the second process chamber 150b.

Although it is not required, the reduced thickness of the area 172a may provide a number of advantages. It may, for example, limit the location or locations in which the lip 170a may be easily pierced to provide the desired opening, i.e., the thicker portions of the lip 170a surrounding the area 172a may be more resistant to piercing by any of the techniques that could be used to pierce the lip 170a to form an opening therethrough. The techniques that could be used to pierce the lip 170a may include, e.g., mechanical piercing (using, e.g., a pin, needle, etc.), laser ablation, etc. Another potential advantage of the area 172a of reduced thickness is that it can be molded into the core layer 180 along with, e.g., the process chambers and distribution channels.

Although devices such as those described herein may be well-suited to performing processes such as e.g., PCR, Sanger sequencing, etc., devices of the invention may be limited to clean-up of the products of such processes which may be performed off of the devices.

Rotation of any device including process arrays such as those depicted in FIGS. 1-4 may be used to facilitate mixing through mechanical agitation of the sample materials and any other materials (e.g., reagents, etc.) present in the process chambers. The mechanical agitation may be accomplished by oscillating the device in opposite directions about the axis of rotation. The oscillations may vary in frequency and/or magnitude depending on a variety of factors, e.g., the size/shape of the process chambers, the amount of materials in the process chambers, viscosities, temperatures, stability of the sample materials, etc. For example, it may be useful to accomplish mixing by oscillating the device 10 at a frequency of about 1 Hertz (Hz) to about 100 Hertz. The magnitude of the oscillations may be, e.g., from about 5 degrees to about 360 degrees.

The mechanical agitation can be carried out during, for example, PCR, Sanger cycling, clean-up of the PCR reaction mixture, clean-up of the sequencing reaction mixture, as well as during various other processes that can be carried out in the microfluidic devices described herein. Similarly, mechanical agitation by rotation, or other means, can be carried out on any of the devices described herein.

EXAMPLES

Objects and advantages of this invention are further illustrated by the following examples, but the particular materials and amounts thereof recited in these examples, as well as other conditions and details, should not be construed to unduly limit this invention.

Example 1

Preparation of Polyquat Film Using a Crosslinker and Polyoxyethylenediamine

Figure 5:
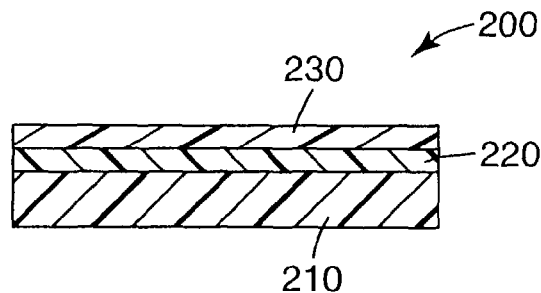
FIG. 5 is a cross-sectional view of one embodiment of a layered coating construction of the present invention.

This example describes the preparation of an article, which is shown in FIG. 5, for use in the methods and devices of the present invention. FIG. 5 is a cross-sectional view of a layered coating construction 200 (e.g., a disk) of the present invention that includes an azlactone-coated polycarbonate film 210, a layer of a crosslinked polyquat/polyoxyethylenediamine 220, and a layer of PSSA 230 for partial passivation of the positive charges of the anion exchange material. This was prepared as follows.

A sample of 0.45 gram of polyoxyethylenediamine (JEFFAMINE XTJ-502 from Huntsman Corporation, Houston, Tex.) was weighed into a 50-ml beaker. Ten (10) ml of 1-methoxy-2-propanol was added to the beaker and was allowed to stir until the polyoxyethylenediamine was completely dissolved. Ten milliliters (10 ml) of trimethyl amino methacrylate/methyl methacrylate (SYNTRAN HX 31-65 from Interpolymer Corp., Canton, Mass.) was added to the solution and was allowed to mix in with the polyoxyethylenediamine solution. Seven (7) drops (approximately 100 microliters) of aliphatic triglycidyl ether (HELOXY Modifier 48 from Resolution Performance Products, Houston, Tex.) was added to the solution to crosslink the amines. Using a transfer pipette, 0.5-1 ml of the above prepared solution was placed on the surface of an azlactone-coated polycarbonate film, which was prepared as described below.

The azlactone was prepared and coated on a polycarbonate film as follows: one (1) gram of a 5% weight by weight (W/W) isopropanol solution of 70:30 dimethyl acrylamide/vinyl dimethyl (DMA/VDM) azlactone copolymer solution was weighed into a 15-ml centrifuge tube. Four (4) grams of isopropanol (IPA) was added. Ninety (90) microliters of IPA was added to a second centrifuge tube. Ten (10) microliters of ethylene diamine (EDA) was added to the second tube. Twelve (12) microliters of the 1:10 dilution of EDA was added to the 1% W/W solution of azlactone and mixed well. Using a No. 14 Meyer bar, the azlactone solution was coated onto the polycarbonate film. After coating, the polycarbonate film was placed in a 40° C. oven for 15 minutes to help crosslink the copolymer.

With a No. 3 Meyer bar, the solution of polyoxyethylenediamine and trimethyl amino methacrylate/methyl methacrylate (0.5-1 ml) was coated across the surface of the zlactone-coated polycarbonate film. Excess solution was removed with a wet paper towel. The coated film was then placed in an aluminum pan and heated at 120° C. for 10 minutes to activate the HELOXY crosslinker and form a crosslinked polyquat/polyoxyethylene diamine. The coating was then placed into a PYREX glass pan and washed for 2.5 hours in 500 ml of deionized water, with 3 water changes over the 2.5 hours. After the film was air dried overnight, 4-millimeter (mm) diameter disks were punched out for placement in a column or microfluidic device.

To determine if the amount of HELOXY crosslinker and JEFFAMINE polyoxyethylenediamine used above was sufficient, the samples were tested in the following manner. The above prepared 4-mm disks were sandwiched between two retainer rings and were placed within a 4-mm diameter column (P/N 78-8095-4502-9, 3M, St. Paul, Minn. 55144). Ten (10) microliters of quarter strength BIGDYE Terminator v 2.0 (Applied Biosystems, Inc., Foster City, Calif.) cycle sequencing reaction containing 2 μL BIGDYE mix, 200 ng DNA template, and 1.6 picomoles of a primer were thermocycled according to manufacturers instructions in a GENEAMP PCR System 9700 thermocycler (Applied Biosystems, Inc.). Five (5) microliters of the above unpurified quarter strength sequencing reaction mixture (containing dye terminators and their hydrolysis products, DNA template, Taq polymerase, buffer, dNTPs, and primer) were introduced into the column. The column was mechanically agitated by shaking it at a frequency of 12-14 Hz with an angular displacement of 20 degrees for a short time (under 10 minutes). The purified reactions were removed from the column and analyzed by Capillary Electrophoresis (CE).

Capillary Electrophoresis analysis of the sequencing reaction mixtures was done with a Beckman P/ACE MDQ Capillary Electrophoresis Instrument (Beckman Coulter, Fullerton, Calif.) with a fluorescence detector (488-nanometer (nm) excitation, 530 nm to 700 nm emission) using a 75-micrometer ID (inner diameter), 30-cm long (20 cm to the detector) fused silica capillary. Runs were performed at 500 volts per centimeter (V/cm) (15 KV total) using 50 millimolar (mM) Tris-HCl/1 mM EDTA (pH 8.5) as the running buffer. Sample injection was done at 690 Pascals for 5 seconds. The conditions used gave good separation of the dye terminators (all the four ddNTPs corresponding to the four bases, A, T, G, C as one peak with a retention time of 3.2 minutes) and its degradation products (as one peak with a retention time of 2.2 minutes) and the combined sequencing ladder (as one peak with a retention time of 4.1 minutes). Sequencing ladder and dye terminator concentrations were obtained by integrating the peak area of the various analytes. For each of the samples, the baseline was subtracted from the analyte values and the resulting analyte concentration was represented as a percentage of the starting sequencing reaction. CE results showed that the dye terminators and its degradation products content was brought down to less than 2% of the original concentration and the DNA content in solution was at least 30% of the starting concentration.

The crosslinked polyquat/polyoxyalkylenediamine films were treated subsequently with various concentrations of PSSA for partial passivation of the positive charges of the anion exchange material to allow for increased recovery of DNA. The films were passivated by using aqueous solutions of sodium salt of PSSA, typically at concentrations from 0.0001 percent by weight (wt-%) to 0.05 wt-%.

Example 2

BIGDYE Terminators v 2.0 Sequencing Reaction Clean-Up with Polyquat/Polyoxyethylenediamine/PSSA Coated Polycarbonate Film in a Microfluidic Device The film prepared and partially passivated with 0.00025 percent by weight (wt-%) PSSA as described in Example 1 was applied to the bottoms of clean-up chambers of a microfluidic disk of the type described in U.S. patent application Publication No. US 2002/0047003 A1 published on Apr. 25, 2002 and entitled ENHANCED SAMPLE PROCESSING DEVICES SYSTEMS AND METHODS. Disks (3.2 mm diameter) of the membrane were positioned onto an adhesive cover film (9795R Advanced Sealing Tape, 3M Medical Specialties, St. Paul, Minn.), which was laminated onto a microfluidic disk, with the membrane registered such that it covered the top bottom of clean-up chambers. Ten (10) microliters of quarter strength BIGDYE Terminator v 2.0 (Applied Biosystems, Inc., Foster City, Calif.) cycle sequencing reaction containing 2 µL BIGDYE mix, 200 ng DNA template, and 1.6 picomoles of a primer were thermocycled according to manufacturers instructions in a GENEAMP PCR System 9700 thermocycler (Applied Biosystems, Inc.). Five (5) microliters of the above unpurified quarter strength sequencing reaction mixture (containing dye terminators and their hydrolysis products, DNA template, Taq polymerase, buffer, dNTPs, and primer) was introduced to the input well and spun into the processing chamber of the microfluidic disk. The microfluidic disk was mechanically agitated by shaking it at a frequency of 12-14 Hz with an angular displacement of 20 degrees for a short time (under 10 minutes). A valve was opened to allow the purified reaction mixture to flow into the next chamber. The purified reactions were removed and analyzed by ABI PRISM 3100 Genetic Analyzer under standard sequencing conditions (Applied Biosystems, Inc.). An excellent electropherogram with no dye blobs was obtained.

Example 3

Polymerase Chain Reaction (PCR) Clean-Up with Polyquat/Polyoxyethylenediamine/PSSA Coated Polycarbonate Film A typical PCR reaction contains 200 nM of each of the two primers and 200 µM of each of the four dNTPs (dGTP, dATP, dCTP, and dTTP). Most of the residual primers and dNTPs after a thermocycling reaction need to be removed because the carry over dNTPs and primers can interfere in subsequent down stream applications such as sequencing reaction. At the same time sufficient amount of PCR product needs to be recovered for further processing. The ability of polyquat/polyoxyethylenediamine film to remove primers and dNTPs, for recovery of PCR amplicons and clean up of a PCR reaction for further processing has been tested as follows.

Figure 6:
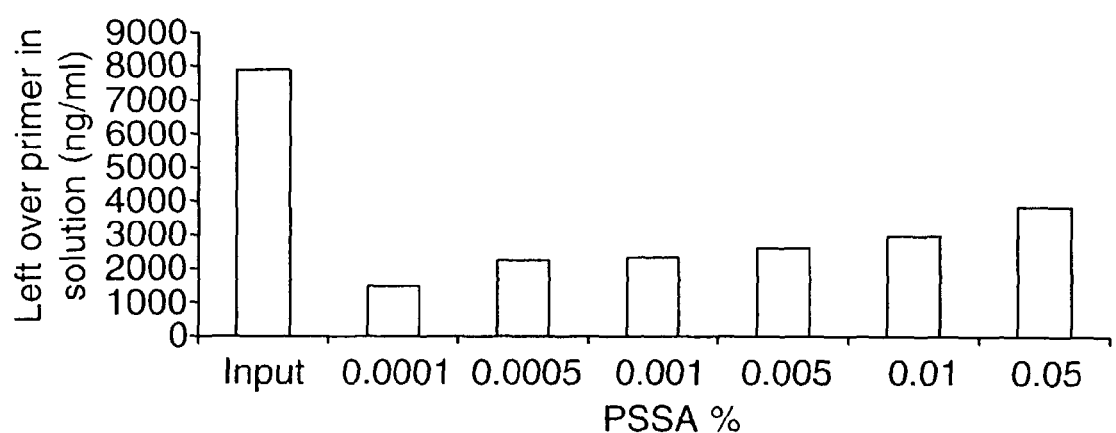
FIG. 6 is a chart of the amount of primer remaining in solution as a function of the amount of poly(sodium 4-styrenesulfonate) or PSSA.
Figure 7:
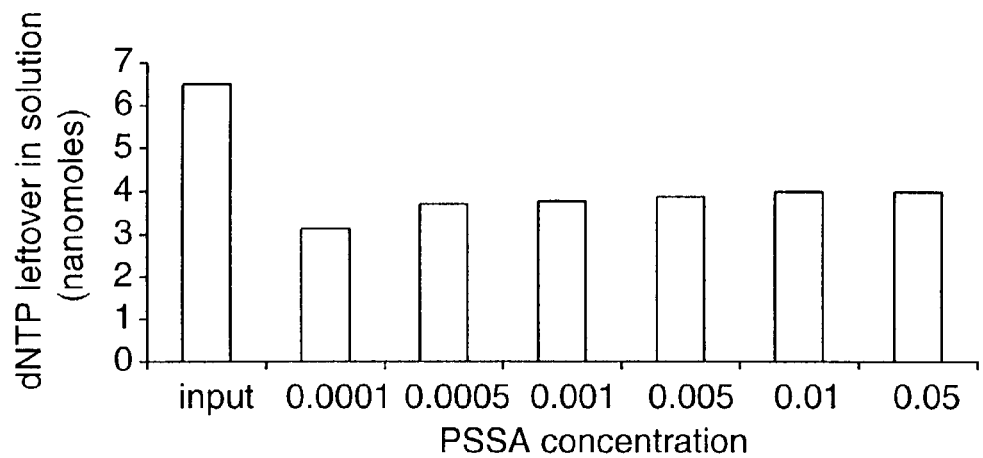
FIG. 7 is a chart of the amount of dNTPs remaining in solution as a function of the amount of PSSA.

Primer Removal. Films prepared and partially passivated with 0.0001-0.05 wt-% PSSA as described in Example 1 were applied to the bottoms of clean-up chambers of a microfluidic disk of the type described in Example 2. A known amount (1 to 10 picomoles) of an oligonucleotide (M13/PUC sequencing primer (−47) (24-mer), New England Biolabs, Beverly, Mass.) in 10 µL 1×PCR buffer (Applied Biosystems, Inc.) was added to the input well and spun into the processing chamber of the microfluidic disk. The processing chamber was mechanically agitated by shaking the microfluidic disk at a frequency of 12-14 Hz with an angular displacement of 20 degrees for a short time (under 10 minutes). A valve was opened to allow the purified reaction mixture to flow into the next chamber. The amount of primers remaining in the eluent was determined using the OLIGREEN ssDNA quantitation reagent (Molecular Probes, Eugene, Oreg.). The amount of primer left over in solution (i.e., not bound to the clean up media) as a function of the amount of PSSA is shown in FIG. 6.

dNTP Removal. Films prepared and partially passivated with 0.0001-0.05 wt-% PSSA as described in Example 1 were applied to the bottoms of clean-up chambers of a microfluidic disk of the type described in Example 2. A known amount of dNTPs (8 nanomoles with equal amounts of each of the four dNTPs) in 10 µL1×PCR buffer (Applied Biosystems, Inc.) was added to the input well and spun into processing chamber of the microfluidic disk. The processing chamber was mechanically agitated by shaking the microfluidic disk at a frequency of 12-14 Hz with an angular displacement of 20 degrees for a short time (under 10 minutes). A valve was opened to allow the purified reaction mixture to flow into the next chamber. The amount of dNTPs remaining in the eluent was determined using absorbance at 260 nm in a spectrophotometer. The amount of dNTPs left over in solution (i.e., not bound to the clean up media) as a function of the amount of PSSA is shown in FIG. 7.

PCR Product Purification in a Microfluidic Disk. Films prepared and partially passivated with 0.0001-0.05 wt-% PSSA as described in Example 1 were applied to the bottoms of clean-up chambers of a microfluidic disk of the type described in Example 2. In this example, 5 µL PCR product (containing 1×PCR buffer, remaining primers, dNTPs, DNA template and Taq polymerase) was added to the input well and spun into a processing chamber of the microfluidic disk. The processing chamber was mechanically agitated by shaking the microfluidic disk at a frequency of 12-14 Hz with an angular displacement of 20 degrees for a short time (under 10 minutes). A valve was opened to allow the purified reaction mixture to flow into the next chamber. The purified PCR amplicons were used for sequencing and purified sequencing reactions were analyzed by ABI PRISM 3100 Genetic Analyzer under standard sequencing conditions (Applied Biosystems, Inc.). The electropherograms yielded excellent sequencing data indicating that the polyquat/PSSA films provided good purification of the PCR amplicons.

Example 4

SNaPshot Reaction Clean-Up with Polyquat/Polyoxyethylenediamine/PSSA Coated Polycarbonate Film SNaPshot chemistry utilizes single-base extension of an unlabelled oligonucleotide primer. Each primer binds to a complimentary template in the presence of fluorescently labeled ddNTPs and the polymerase extends the primer by one nucleotide adding a single ddNTP to its 3' end. The products of the reactions are separated by electrophoresis and alleles are identified using the incorporated ddNTP. It is important to remove the unincorporated ddNTPs for accurate base calling, as the mobility of free dyes interfere with separation of DNA of interest. The kit is designed to interrogate up to ten single nucleotide polymorphisms (SNPs) at known locations on one to ten DNA templates in a single tube.

Figure 8:
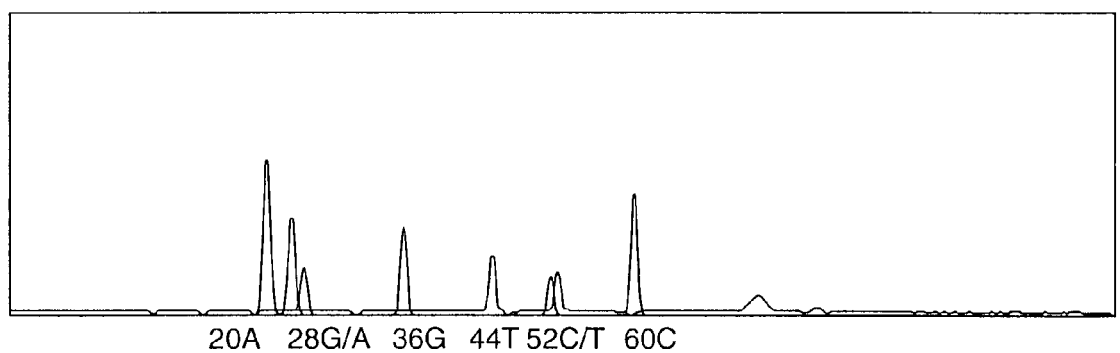
FIG. 8 is an electropherogram of a reaction mixture after being subjected to a method of the present invention.

Five microliters (5 µL) quarter strength multiplex SNaPshot reaction (Applied Biosystems, Inc.) containing 0.625 µL SNaPshot mix, PCR product, and 200 nM of each of the primers were thermocycled according to manufacturers instructions in a GENEAMP PCR System 9700 thermocycler (Applied Biosystems, Inc). Five microliters (5 µL) of the above unpurified quarter strength reaction mixture (containing dye terminators and their hydrolysis products, DNA template, Taq polymerase, buffer, and primer) was introduced into a 4-mm diameter column containing the polyquat/polyoxyalkylenediamine disk partially passivated with 0.00025 wt-% PSSA as prepared in Example 1. The column was mechanically agitated by shaking at a frequency of 12-14 Hz with an angular displacement of 20 degrees for a short time (under 10 minutes). The purified reactions were removed from the column and analyzed by ABI PRISM 310 Genetic Analyzer (Applied Biosystems, Inc.). The electropherogram shown in FIG. 8 indicates that the genotype could be accurately called.

Example 5

Sequencing Reaction Clean-Up with and without Polyoxyethylenediamine

Polyquat/polyoxyalkylenediamine films partially passivated with 0.00025 wt-% PSSA as prepared in Example 1 were made into disks according to the procedure in Example 2. Additionally, polyquat films disks were made by the same process and materials, but without the polyoxyethylenediamine and used for comparative testing.

Ten (10) microliters of quarter strength BIGDYE Terminator v 2.0 (Applied Biosystems, Inc., Foster City, Calif.) cycle sequencing reaction containing 2 µL BIGDYE mix, 200 ng DNA template, and 1.6 picomoles of a primer were thermocycled according to manufacturers instructions in a GENEAMP PCR System 9700 thermocycler (Applied Biosystems, Inc.). Five (5) microliters of the above unpurified quarter strength sequencing reaction mixture (containing dye terminators and their hydrolysis products, DNA template, Taq polymerase, buffer, dNTPs and primer) was introduced into a column containing the polyquat film disks and were mechanically agitated by shaking the disks at a frequency of 12-14 Hz with an angular displacement of 20 degrees for a short time (under 10 minutes). The purified reactions were removed from the column and analyzed by Capillary Electrophoresis.

Capillary electrophoresis analysis of the sequencing reactions was done with a Beckman P/ACE MDQ Capillary Electrophoresis instrument (Beckman Coulter, Fullerton, Calif.) with a fluorescence detector (488-nanometer (nm) excitation, 530 nm to 700 nm emission) using a 75 micrometer ID, 30 cm long (20 cm to the detector) fused silica capillary. Runs were performed at 500 volts per centimeter (V/cm) (15 KV total) using 50 millimolar (mM) Tris-HCl/1 mM EDTA (pH 8.5) as the running buffer. Sample injection was done at 690 Pascals for 5 seconds. The conditions used gave good separation of the dye terminators (all the four ddNTPs corresponding to the four bases, A, T, G, C as one peak with a retention time of 3.2 minutes) and its degradation products (as one peak with a retention time of 2.2 minutes) and the combined sequencing ladder (as one peak with a retention time of 4.1 minutes). Sequencing ladder and dye terminator concentrations were obtained by integrating the peak area of the various analytes. For each of the samples, the baseline was subtracted from the analyte values and the resulting analyte concentration was represented as a percentage of the starting sequencing reaction. CE results showed that the disks containing polyoxyethylenediamine removed a greater amount of the dye terminators and its degradation products than disks not containing polyoxyethylenediame.

Patents, patent applications, and publications disclosed herein are hereby incorporated by reference (in their entirety) as if individually incorporated. It is to be understood that the above description is intended to be illustrative, and not restrictive. Various modifications and alterations of this invention will become apparent to those skilled in the art from the foregoing description without departing from the scope of this invention, and it should be understood that this invention is not to be unduly limited to the illustrative embodiments set forth herein.

What is claimed is:

1. A method of removing small negatively charged organic molecules from a biological sample mixture, the method comprising:
   providing a surface comprising an anion exchange material partially coated with a negatively charged polymer prior to contact with a biological sample mixture, wherein the anion exchange material is mixed with a polyoxyalkylene;
   providing a biological sample mixture; and
   contacting the biological sample mixture with the surface comprising an anion exchange material partially coated with a negatively charged polymer to remove at least a portion of the small negatively charged organic molecules from the biological sample mixture.

2. The method of claim 1 wherein the polyoxyalkylene is a nucleophilic polyoxyalkylene.

3. The method of claim 2 wherein the nucleophilic polyoxyalkylene is crosslinked.

4. The method of claim 1 wherein the negatively charged polymer is a polyelectrolyte.

5. The method of claim 4 wherein the negatively charged polyelectrolyte is selected from the group consisting of a polystyrene sulfonic acid, polyvinyl phosphonic acid, polyvinyl boric acid, polyvinyl sulfonic acid, polyvinyl sulfuric acid, polystyrene phosphonic acid, polyacrylic acid, polymethacrylic acid, lignosulfonate, carrageenan, heparin, chondritin sulfate, salts thereof, and mixtures thereof.

6. The method of claim 1 wherein the anion exchange material comprises quaternized, nitrogen.

7. The method of claim 1 wherein the biological sample mixture is a nucleic acid sequencing reaction mixture.

8. The method of claim 7 wherein the small negatively charged organic molecules are selected from the group consisting of dye-labeled terminators, primers, degraded dye molecules, deoxynucleotide triphosphates, and mixtures thereof.

9. The method of claim 8 wherein the small negatively charged organic molecules comprise dye-labeled terminators.

10. The method of claim 9 wherein the dye-labeled terminators are selected from the group consisting of dideoxynucleotide triphosphates, dideoxynucleotide diphosphates, dideoxynucleotide monophosphates, dideoxynucleosides, and combinations thereof.

11. The method of claim 10 wherein contacting the biological sample mixture with the surface comprising an anion exchange material partially coated with a negatively charged polymer is carried out under conditions effective to remove substantially all the dye-labeled terminators from the biological sample mixture.

12. The method of claim 1 wherein the biological sample mixture is a PCR reach on mixture.

13. The method of claim 12 wherein the small negatively charged organic molecules are selected from the group consisting of primers, degraded dye molecules, deoxynucleotide triphosphates, and mixtures thereof.

14. The method of claim 13 wherein contacting the biological sample mixture with the surface comprising an anion exchange material partially coated with a negatively charged polymer is carried out under conditions effective to remove substantially all the primers from the biological sample mixture.

15. The method of claim 1 wherein the small negatively charged organic molecules have a molecular weight of less than 6,000.

16. The method of claim 1 wherein contacting the biological sample mixture with the surface comprising an anion exchange material partially coated with a negatively charged polymer comprises agitating while contacting.

17. The method of claim 1 which is carried out in a microfluidic device.

18. A method of removing small negatively charged organic molecules from a biological sample mixture, the method comprising:
providing a surface comprising an anion exchange material comprising quaternary ammonium ions partially coated with a negatively charged polyelectrolyte prior to contact with a biological sample mixture, wherein the anion exchange material is mixed with a polyoxyalkylene;
providing a biological sample mixture; and
contacting the biological sample mixture with the surface comprising quaternary ammonium ions partially coated with a negatively charged polyelectrolyte to remove at least a portion of the small negatively charged organic molecules from the biological sample mixture.

19. The method of claim 18 wherein the polyoxyalkylene is a nucleophilic polyoxyalkylene.

20. The method of claim 19 wherein the nucleophilic polyoxyalkylene is crosslinked.

21. A method of removing small negatively charged organic molecules from a biological sample mixture, the method comprising:
providing a surface comprising an anion exchange material comprising quaternary ammonium ions partially coated with a negatively charged polyelectrolyte prior to contact with a biological sample mixture, wherein the anion exchange material is mixed with a polyoxyalkylene;
providing a biological sample mixture; and
contacting the biological sample mixture with the surface comprising quaternary ammonium ions partially coated with a negatively charged polyelectrolyte to remove at least a portion of the small negatively charged organic molecules from the biological sample mixture;
wherein the biological sample mixture comprises a nucleic acid amplification reaction mixture.

22. The method of claim 21 wherein the polyoxyalkylene is a nucleophilic polyoxyalkylene.

23. The method of claim 22 wherein the nucleophilic polyoxyalkylene is crosslinked.

24. The method of claim 21 which is carried out in a microfluidic device.

25. A method of removing small negatively charged organic molecules from a biological sample mixture, the method comprising:
providing a device comprising at least one process array that comprises a nonporous surface comprising an anion exchange material partially coated with a negatively charged polymer prior to contact with a biological sample mixture, wherein the anion exchange material has associated therewith a polyoxyalkylene;
providing a biological sample mixture in the at least one process array; and
transferring the biological sample mixture within the at least one process array, wherein the biological sample mixture and the surface comprising an anion exchange material partially coated with a negatively charged polymer remain in contact for a sufficient time to remove at least a portion of the small negatively charged organic molecules from the biological sample mixture.

26. The method of claim 25 wherein the polyoxyalkylene is a nucleophilic polyoxyalkylene.

27. The method of claim 26 wherein the nucleophilic polyoxyalkylene is crosslinked.

28. The method of claim 25 wherein the negatively charged polymer is a polyelectrolyte.

29. The method of claim 28 wherein the negatively charged polyelectrolyte is selected from the group consisting of a polystyrene sulfonic acid, polyvinyl phosphonic acid, polyvinyl boric acid, polyvinyl sulfonic acid, polyvinyl sulfuric acid, polystyrene phosphonic acid, polyacrylic acid, polymethacrylic acid, lignosulfonate, carrageenan, heparin, chondritin sulfate, salts thereof, and mixtures thereof.

30. The method of claim 25 wherein the anion exchange material comprises quaternary ammonium ions.

31. The method of claim 25 wherein the biological sample mixture is a nucleic acid sequencing reaction mixture.

32. The method of claim 31 wherein the small negatively charged organic molecules are selected from the group consisting of dye-labeled terminators, primers, degraded dye molecules, deoxynucleotide triphosphates, and mixtures thereof.

33. The method of claim 32 wherein the small negatively charged organic molecules comprise dye-labeled terminators.

34. The method of claim 33 wherein the dye-labeled terminators are selected from the group consisting of dideoxynucleotide triphosphates, dideoxynucleotide diphosphates, dideoxynucleotide monophosphates, dideoxynucleosides, and combinations thereof.

35. The method of claim 34 wherein the biological sample mixture and the surface comprising an anion exchange material partially coated with a negatively charged polymer are contacted under conditions effective to remove substantially all the dye-labeled terminators from the biological sample mixture.

36. The method of claim 25 wherein the biological sample mixture is a PCR reaction mixture.

37. The method of claim 36 wherein the small negatively charged organic molecules are selected from the group consisting of primers, degraded dye molecules, deoxynucleotide triphosphates, and mixtures thereof.

38. The method of claim 37 wherein the biological sample mixture and the surface comprising an anion exchange material partially coated with a negatively charged polymer are contacted under conditions effective to remove substantially all the primers from the biological sample mixture.

39. The method of claim 25 wherein the small negatively charged organic molecules have a molecular weight of less than 6,000.

40. The method of claim 25 wherein the biological sample mixture and the surface comprising an anion exchange material partially coated with a negatively charged polymer are agitated while in contact.

41. The method of claim 25 wherein the at least one process array comprises a loading chamber, at least one process chamber, and at least one distribution channel connecting the loading chamber and the at least one process chamber.

42. A method of removing small negatively charged organic molecules from a biological sample mixture, the method comprising:
providing a device comprising at least one process array that comprises a nonporous surface comprising an anion exchange material comprising quaternary ammonium ions partially coated with a negatively charged polyelectrolyte prior to contact with a biological sample mixture, wherein the anion exchange material has associated therewith a polyoxyalkylene;

providing a biological sample mixture in the at least one process array; and transferring the biological sample mixture within the at least one process array, wherein the biological sample mixture and the surface comprising quaternary ammonium ions partially coated with a negatively charged polyelectrolyte remain in contact for a sufficient time to remove at least a portion of the small negatively charged organic molecules from the biological sample mixture.

43. The method of claim 42 wherein the polyoxyalkylene is a nucleophilic polyoxyalkylene.

44. The method of claim 43 wherein the nucleophilic polyoxyalkylene is crosslinked.

45. The method of claim 42 wherein the biological sample mixture comprises a nucleic acid amplification reaction mixture.

46. The method of claim 42 wherein the biological sample mixture and the surface comprising quaternary ammonium ions partially coated with a negatively charged polyelectrolyte are agitated while in contact.

47. The method of claim 1 wherein the small negatively charged organic molecules have a molecular weight of less than 6,000 and are selectively removed from organic molecules having a molecular weight of greater than 8,000.

48. The method of claim 18 wherein the small negatively charged organic molecules have a molecular weight of less than 6,000 and are selectively removed from organic molecules having a molecular weight of greater than 8,000.

49. The method of claim 21 wherein the small negatively charged organic molecules have a molecular weight of less than 6,000 and are selectively removed from organic molecules having a molecular weight of greater than 8,000.

50. The method of claim 25 wherein the small negatively charged organic molecules have a molecular weight of less than 6,000 and are selectively removed from organic molecules having a molecular weight of greater than 8,000.

51. The method of claim 42 wherein the small negatively charged organic molecules have a molecular weight of less than 6,000 and are selectively removed from organic molecules having a molecular weight of greater than 8,000.

* * * * *

UNITED STATES PATENT AND TRADEMARK OFFICE
CERTIFICATE OF CORRECTION

| | | |
|---|---|---|
| PATENT NO. | : 7,981,600 B2 | |
| APPLICATION NO. | : 10/417609 | |
| DATED | : July 19, 2011 | |
| INVENTOR(S) | : Ranjani V Parthasarathy | |

It is certified that error appears in the above-identified patent and that said Letters Patent is hereby corrected as shown below:

Column 21
Line 63-64, Delete "zlactone-coated" and insert -- azlactone-coated --, therefor.

Column 26
Line 34, In Claim 6, delete "quaternized," and insert -- quaternized --, therefor.

Signed and Sealed this
Thirteenth Day of September, 2011

David J. Kappos
*Director of the United States Patent and Trademark Office*